US011691015B2

(12) United States Patent
Minassian et al.

(10) Patent No.: US 11,691,015 B2
(45) Date of Patent: Jul. 4, 2023

(54) SYSTEM FOR NEUROMODULATION

(71) Applicant: ONWARD MEDICAL N.V., Eindhoven (NL)

(72) Inventors: Karen Minassian, Vienna (AT); Fabien Wagner, Lausanne (CH); Grégoire Courtine, Lausanne (CH)

(73) Assignee: Onward Medical N.V., Eindhoven (NL)

( * ) Notice: Subject to any disclaimer, the term of this patent is extended or adjusted under 35 U.S.C. 154(b) by 127 days.

(21) Appl. No.: 17/033,431

(22) Filed: Sep. 25, 2020

(65) Prior Publication Data
US 2021/0016093 A1 Jan. 21, 2021

Related U.S. Application Data

(63) Continuation of application No. 15/989,726, filed on May 25, 2018, now Pat. No. 10,799,702.

(30) Foreign Application Priority Data

Jun. 30, 2017 (EP) .................................... 17178950

(51) Int. Cl.
*A61N 1/36* (2006.01)
*A61N 1/05* (2006.01)

(52) U.S. Cl.
CPC ..... *A61N 1/36146* (2013.01); *A61N 1/36003* (2013.01); *A61N 1/36062* (2017.08);
(Continued)

(58) Field of Classification Search
CPC .............. A61N 1/0553; A61N 1/36003; A61N 1/3605; A61N 1/36057; A61N 1/36062;
(Continued)

(56) References Cited

U.S. PATENT DOCUMENTS 3,543,761 A 12/1970 Bradley
3,650,277 A 3/1972 Sjostrand et al.
(Continued)

FOREIGN PATENT DOCUMENTS

AU 2012204526 B2 7/2012
CA 2823592 A1 7/2012
(Continued)

OTHER PUBLICATIONS

Guyatt, G. et al., "The 6-minute walk: a new measure of exercise capacity in patients with chronic heart failure," Canadian Medical Association Journal, vol. 132, No. 8, Apr. 15, 1985, 5 pages.
(Continued)

*Primary Examiner* — Brian T Gedeon
(74) *Attorney, Agent, or Firm* — Finnegan, Henderson, Farabow, Garrett & Dunner, LLP

(57) ABSTRACT

The present disclosure relates to a system for neuromodulation and/or neurostimulation, for the treatment of a subject. The system comprises a stimulation controller, a stimulation pattern storage means including stimulation data connected to the stimulation controller, an electrical stimulation device and electrical interface between the electrical stimulation device and the subject, the electrical interface being connectable with a bio-interface of the nervous system of the subject. The stimulation data are pre-programmed patterns comprising spatial and temporal components, The stimulation controller sends configuration signals on the basis of the stimulation data to the electrical stimulation device such that via the electrical interface electrical stimulation is provided to the bio-interface, wherein the electrical stimulation provided is characterized by stimulation parameters that vary over time in a pre-programmed manner.

17 Claims, 12 Drawing Sheets

(52) U.S. Cl.
CPC ..... *A61N 1/36067* (2013.01); *A61N 1/36157* (2013.01); *A61N 1/36171* (2013.01); *A61N 1/36175* (2013.01); *A61N 1/0553* (2013.01)

(58) Field of Classification Search
CPC ............ A61N 1/36128; A61N 1/36146; A61N 1/36157; A61N 1/36171; A61N 1/36175
See application file for complete search history.

(56) References Cited

U.S. PATENT DOCUMENTS

| | | | |
|---|---|---|---|
| 3,662,758 A | 5/1972 | Glover | |
| 3,724,467 A | 4/1973 | Avery et al. | |
| 4,044,774 A | 8/1977 | Corbin et al. | |
| 4,102,344 A | 7/1978 | Conway et al. | |
| 4,141,365 A | 2/1979 | Fischell et al. | |
| 4,285,347 A | 8/1981 | Hess | |
| 4,340,063 A | 7/1982 | Maurer | |
| 4,379,462 A | 4/1983 | Borkan et al. | |
| 4,398,537 A | 8/1983 | Holmbo | |
| 4,414,986 A | 11/1983 | Dickhudt et al. | |
| 4,538,624 A | 9/1985 | Tarjan | |
| 4,549,556 A | 10/1985 | Tarjan et al. | |
| 4,559,948 A | 12/1985 | Liss et al. | |
| 4,569,352 A | 2/1986 | Petrofsky et al. | |
| 4,573,481 A | 3/1986 | Bullara | |
| 4,724,842 A | 2/1988 | Charters | |
| 4,800,898 A | 1/1989 | Hess et al. | |
| 4,934,368 A | 6/1990 | Lynch | |
| 4,969,452 A | 11/1990 | Petrofsky et al. | |
| 5,002,053 A | 3/1991 | Garcia-Rill et al. | |
| 5,031,618 A | 7/1991 | Mullet | |
| 5,066,272 A | 11/1991 | Eaton et al. | |
| 5,081,989 A | 1/1992 | Graupe et al. | |
| 5,121,754 A | 6/1992 | Mullett | |
| 5,344,439 A | 9/1994 | Otten | |
| 5,354,320 A | 10/1994 | Schaldach et al. | |
| 5,366,813 A | 11/1994 | Berlin | |
| 5,374,285 A | 12/1994 | Vaiani et al. | |
| 5,417,719 A | 5/1995 | Hull et al. | |
| 5,476,441 A | 12/1995 | Durfee et al. | |
| 5,562,718 A | 10/1996 | Palermo | |
| 5,643,330 A | 7/1997 | Holsheimer et al. | |
| 5,733,322 A | 3/1998 | Starkebaum | |
| 5,983,141 A | 11/1999 | Sluijter et al. | |
| 6,058,331 A | 5/2000 | King | |
| 6,066,163 A | 5/2000 | John | |
| 6,104,957 A | 8/2000 | Alo et al. | |
| 6,122,548 A | 9/2000 | Starkebaum et al. | |
| 6,308,103 B1 | 10/2001 | Gielen | |
| 6,319,241 B1 | 11/2001 | King et al. | |
| 6,463,327 B1 | 10/2002 | Lurie et al. | |
| 6,470,213 B1 | 10/2002 | Alley | |
| 6,500,110 B1 | 12/2002 | Davey et al. | |
| 6,503,231 B1 | 1/2003 | Prausnitz et al. | |
| 6,505,074 B2 | 1/2003 | Boveia et al. | |
| 6,516,227 B1 | 2/2003 | Meadows et al. | |
| 6,551,849 B1 | 4/2003 | Kenney | |
| 6,587,724 B2 | 7/2003 | Mann | |
| 6,662,053 B2 | 12/2003 | Borkan | |
| 6,666,831 B1 | 12/2003 | Edgerton et al. | |
| 6,685,729 B2 | 2/2004 | Gonzalez | |
| 6,748,276 B1 | 6/2004 | Daignault, Jr. et al. | |
| 6,819,956 B2 | 11/2004 | DiLorenzo | |
| 6,839,594 B2 | 1/2005 | Cohen et al. | |
| 6,862,479 B1 | 3/2005 | Whitehurst et al. | |
| 6,871,099 B1 | 3/2005 | Whitehurst et al. | |
| 6,878,112 B2 | 4/2005 | Linberg et al. | |
| 6,892,098 B2 | 5/2005 | Ayal et al. | |
| 6,895,280 B2 | 5/2005 | Meadows et al. | |
| 6,895,283 B2 | 5/2005 | Erickson et al. | |
| 6,937,891 B2 | 8/2005 | Leinders et al. | |
| 6,950,706 B2 | 9/2005 | Rodriguez et al. | |
| 6,975,907 B2 | 12/2005 | Zanakis et al. | |
| 6,988,006 B2 | 1/2006 | King et al. | |
| 6,999,820 B2 | 2/2006 | Jordan | |
| 7,020,521 B1 | 3/2006 | Brewer et al. | |
| 7,024,247 B2 | 4/2006 | Gliner et al. | |
| 7,035,690 B2 | 4/2006 | Goetz | |
| 7,047,084 B2 | 5/2006 | Erickson et al. | |
| 7,065,408 B2 | 6/2006 | Herman et al. | |
| 7,096,070 B1 | 8/2006 | Jenkins et al. | |
| 7,110,820 B2 | 9/2006 | Tcheng et al. | |
| 7,127,287 B2 | 10/2006 | Duncan et al. | |
| 7,127,296 B2 | 10/2006 | Bradley | |
| 7,127,297 B2 | 10/2006 | Law et al. | |
| 7,149,773 B2 | 12/2006 | Haller et al. | |
| 7,153,242 B2 | 12/2006 | Goffer | |
| 7,184,837 B2 | 2/2007 | Goetz | |
| 7,200,443 B2 | 4/2007 | Faul | |
| 7,209,787 B2 | 4/2007 | DiLorenzo | |
| 7,228,179 B2 | 6/2007 | Van Campen et al. | |
| 7,239,920 B1 | 7/2007 | Thacker et al. | |
| 7,251,529 B2 | 7/2007 | Greenwood-Van Meerveld | |
| 7,252,090 B2 | 8/2007 | Goetz | |
| 7,313,440 B2 | 12/2007 | Miesel | |
| 7,324,853 B2 | 1/2008 | Ayal et al. | |
| 7,330,760 B2 | 2/2008 | Heruth et al. | |
| 7,337,005 B2 | 2/2008 | Kim et al. | |
| 7,337,006 B2 | 2/2008 | Kim et al. | |
| 7,340,298 B1 | 3/2008 | Barbut | |
| 7,377,006 B2 | 5/2008 | Genoa et al. | |
| 7,381,192 B2 | 6/2008 | Brodard et al. | |
| 7,415,309 B2 | 8/2008 | McIntyre | |
| 7,463,927 B1 | 12/2008 | Chaouat | |
| 7,463,928 B2 | 12/2008 | Lee et al. | |
| 7,467,016 B2 | 12/2008 | Colborn | |
| 7,493,170 B1 | 2/2009 | Segel et al. | |
| 7,496,404 B2 | 2/2009 | Meadows et al. | |
| 7,502,652 B2 | 3/2009 | Gaunt et al. | |
| 7,536,226 B2 | 5/2009 | Williams et al. | |
| 7,544,185 B2 | 6/2009 | Bengtsson | |
| 7,584,000 B2 | 9/2009 | Erickson | |
| 7,590,454 B2 | 9/2009 | Garabedian et al. | |
| 7,603,178 B2 | 10/2009 | North et al. | |
| 7,620,502 B2 | 11/2009 | Selifonoy et al. | |
| 7,628,750 B2 | 12/2009 | Cohen et al. | |
| 7,647,115 B2 | 1/2010 | Levin et al. | |
| 7,660,636 B2 | 2/2010 | Castel et al. | |
| 7,697,995 B2 | 4/2010 | Cross, Jr. et al. | |
| 7,725,193 B1 | 5/2010 | Chu | |
| 7,729,781 B2 | 6/2010 | Swoyer et al. | |
| 7,734,340 B2 | 6/2010 | de Ridder | |
| 7,734,351 B2 | 6/2010 | Testerman et al. | |
| 7,742,037 B2 | 6/2010 | Sako et al. | |
| 7,769,463 B2 | 8/2010 | Katsnelson | |
| 7,797,057 B2 | 9/2010 | Harris | |
| 7,801,601 B2 | 9/2010 | Maschino et al. | |
| 7,813,803 B2 | 10/2010 | Heruth et al. | |
| 7,813,809 B2 | 10/2010 | Strother et al. | |
| 7,856,264 B2 | 12/2010 | Firlik et al. | |
| 7,877,146 B2 | 1/2011 | Rezai et al. | |
| 7,890,182 B2 | 2/2011 | Parramon et al. | |
| 7,949,395 B2 | 5/2011 | Kuzma | |
| 7,949,403 B2 | 5/2011 | Palermo et al. | |
| 7,987,000 B2 | 7/2011 | Moffitt et al. | |
| 7,991,465 B2 | 8/2011 | Bartic et al. | |
| 8,019,427 B2 | 9/2011 | Moffitt | |
| 8,050,773 B2 | 11/2011 | Zhu | |
| 8,108,051 B2 | 1/2012 | Cross, Jr. et al. | |
| 8,108,052 B2 | 1/2012 | Boling | |
| 8,131,358 B2 | 3/2012 | Moffitt et al. | |
| 8,135,473 B2 | 3/2012 | Miesel et al. | |
| 8,155,750 B2 | 4/2012 | Jaax et al. | |
| 8,168,481 B2 | 5/2012 | Hanaoka et al. | |
| 8,170,660 B2 | 5/2012 | Dacey, Jr. et al. | |
| 8,190,262 B2 | 5/2012 | Gerber et al. | |
| 8,195,304 B2 | 6/2012 | Strother et al. | |
| 8,214,048 B1 | 7/2012 | Whitehurst et al. | |
| 8,229,565 B2 | 7/2012 | Kim et al. | |
| 8,239,038 B2 | 8/2012 | Wolf, II | |
| 8,260,436 B2 | 9/2012 | Gerber et al. | |
| 8,271,099 B1 | 9/2012 | Swanson | |
| 8,295,936 B2 | 10/2012 | Wahlstrand et al. | |

(56) References Cited

U.S. PATENT DOCUMENTS

| | | |
|---|---|---|
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | de Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,626,300 B2 | 1/2014 | Demarais et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,802,052 B2 | 10/2017 | Marnfeldt |
| 9,895,545 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | De Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0029391 A1 | 12/2007 | Strother et al. |
| 2008/0002227 A1 | 1/2008 | Tsujimoto |

(56) References Cited

U.S. PATENT DOCUMENTS

| | | |
|---|---|---|
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0279896 A1 | 11/2008 | Heinen et al. |
| 2008/0294211 A1 | 11/2008 | Moffitt |
| 2008/0294226 A1 | 11/2008 | Moffitt |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0229166 A1 | 9/2009 | Sawrie |
| 2009/0204173 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0010646 A1 | 1/2010 | Drew et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0022831 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Carbunaru et al. |
| 2011/0009919 A1 | 1/2011 | Basak et al. |
| 2011/0029044 A1 | 1/2011 | Peschke et al. |
| 2011/0016081 A1 | 2/2011 | Walker et al. |
| 2011/0029040 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0230747 A1 | 9/2011 | Marino |
| 2011/0230808 A1 | 9/2011 | Prakash et al. |
| 2011/0237921 A1 | 9/2011 | Askin et al. |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | Dilorenzo |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0271372 A1 | 10/2012 | Osorio |

(56) References Cited

U.S. PATENT DOCUMENTS

| | | |
|---|---|---|
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0253222 A1 | 8/2013 | Cullen et al. |
| 2013/0211477 A1 | 9/2013 | Nakao |
| 2013/0237948 A1 | 9/2013 | Sawant et al. |
| 2013/0253229 A1 | 9/2013 | Donders et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0031893 A1 | 1/2014 | Walker et al. |
| 2014/0046407 A1 | 2/2014 | Ben-Ezra et al. |
| 2014/0058292 A1 | 2/2014 | Alford et al. |
| 2014/0058490 A1 | 2/2014 | DiMarco |
| 2014/0066950 A1 | 3/2014 | MacDonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0172045 A1 | 6/2014 | Yip et al. |
| 2014/0180361 A1 | 6/2014 | Burdick et al. |
| 2014/0213842 A1 | 7/2014 | Simon et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon de Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziaie et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0143588 A1 | 5/2016 | Hoitink et al. |
| 2016/0157389 A1 | 6/2016 | Hwang |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0263376 A1* | 9/2016 | Yoo .................... A61N 1/0556 |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2017/0007320 A1 | 1/2017 | Levin et al. |
| 2017/0007831 A1 | 1/2017 | Edgerton et al. |
| 2017/0128729 A1 | 5/2017 | Netoff et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0354819 A1 | 12/2017 | Bloch et al. |
| 2017/0361093 A1 | 12/2017 | Yoo et al. |
| 2018/0056078 A1 | 3/2018 | Kashyap et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0125416 A1 | 5/2018 | Schwarz et al. |
| 2018/0178008 A1 | 6/2018 | Bouton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0280693 A1 | 10/2018 | Edgerton et al. |
| 2018/0353755 A1 | 12/2018 | Edgerton et al. |
| 2018/0361146 A1 | 12/2018 | Gerasimenko et al. |
| 2019/0009094 A1 | 1/2019 | Chang et al. |
| 2019/0022371 A1 | 1/2019 | Olgun et al. |
| 2019/0033622 A1 | 1/2019 | Zhang et al. |
| 2019/0160294 A1 | 5/2019 | Peterson et al. |
| 2019/0167987 A1 | 6/2019 | Lu et al. |
| 2019/0192864 A1 | 6/2019 | Koop et al. |
| 2019/0247650 A1 | 8/2019 | Tran |
| 2019/0262609 A1 | 8/2019 | Brill et al. |
| 2019/0269917 A1 | 9/2019 | Courtine et al. |

(56) References Cited

U.S. PATENT DOCUMENTS

| | | |
|---|---|---|
| 2019/0381313 A1 | 12/2019 | Lu |
| 2019/0381328 A1 | 12/2019 | Wechter et al. |
| 2020/0155865 A1 | 5/2020 | Lu |
| 2020/0228901 A1 | 7/2020 | Baek |
| 2021/0069052 A1 | 3/2021 | Burke |
| 2021/0187278 A1 | 6/2021 | Lu |
| 2021/0236837 A1 | 8/2021 | Lu |
| 2021/0378991 A1 | 12/2021 | Lu et al. |

FOREIGN PATENT DOCUMENTS

| | | | |
|---|---|---|---|
| CA | 2856202 A1 | 5/2013 | |
| CA | 2864473 A1 | 5/2013 | |
| CN | 101227940 A | 7/2008 | |
| CN | 103263727 A | 8/2013 | |
| CN | 104307098 A | 1/2015 | |
| EP | 0630987 A1 | 12/1994 | |
| EP | 2130326 A1 | 12/2009 | |
| EP | 2141851 A2 | 1/2010 | |
| EP | 2160127 A1 | 3/2010 | |
| EP | 2178319 A1 | 4/2010 | |
| EP | 2192897 A1 | 6/2010 | |
| EP | 2226114 A1 | 9/2010 | |
| EP | 2258496 A1 | 12/2010 | |
| EP | 2361631 A1 | 8/2011 | |
| EP | 2368401 A1 | 9/2011 | |
| EP | 2387467 A1 | 11/2011 | |
| EP | 2396995 A1 | 12/2011 | |
| EP | 2397788 A1 | 12/2011 | |
| EP | 2445990 A2 | 5/2012 | |
| EP | 2471518 A2 | 7/2012 | |
| EP | 2475283 A1 | 7/2012 | |
| EP | 2486897 A2 | 8/2012 | |
| EP | 2626051 A1 | 8/2013 | |
| EP | 2628502 A1 | 8/2013 | |
| EP | 2661307 A2 | 11/2013 | |
| EP | 2688642 A2 | 1/2014 | |
| EP | 2810689 A1 | 12/2014 | |
| EP | 2810690 A1 | 12/2014 | |
| EP | 2868343 A1 | 5/2015 | |
| EP | 2966422 A1 | 1/2016 | |
| EP | 2968940 A1 | 1/2016 | |
| EP | 3184145 A1 | 6/2017 | |
| EP | 3323468 A1 | 5/2018 | |
| EP | 3328481 A1 | 6/2018 | |
| EP | 3527258 A1 | 8/2019 | |
| JP | H0326620 A | 2/1991 | |
| JP | 3184145 B2 | 7/2001 | |
| JP | 2002200178 A | 7/2002 | |
| JP | 2004065529 A | 3/2004 | |
| JP | 2007526798 A | 9/2007 | |
| JP | 2008067917 A | 3/2008 | |
| JP | 2008543429 A | 12/2008 | |
| JP | 2014514043 A | 6/2014 | |
| JP | 2016506255 A | 3/2016 | |
| JP | 6132856 B2 | 5/2017 | |
| JP | 2017104685 A | 6/2017 | |
| JP | 2017525509 A | 9/2017 | |
| JP | 2018524113 A | 8/2018 | |
| RU | 2130326 C1 | 5/1999 | |
| RU | 2141851 C1 | 11/1999 | |
| RU | 2160127 C1 | 12/2000 | |
| RU | 2178319 C2 | 1/2002 | |
| RU | 2192897 C2 | 11/2002 | |
| RU | 2001102533 A | 11/2002 | |
| RU | 2226114 C1 | 3/2004 | |
| RU | 2258496 C2 | 8/2005 | |
| RU | 2361631 C2 | 7/2009 | |
| RU | 2368401 C1 | 9/2009 | |
| RU | 2387467 C1 | 4/2010 | |
| RU | 2397788 C2 | 5/2010 | |
| RU | 2396995 C2 | 8/2010 | |
| RU | 2445990 C1 | 3/2012 | |
| RU | 2471518 C2 | 1/2013 | |
| RU | 2475283 C2 | 2/2013 | |
| RU | 2661307 C1 | 7/2018 | |
| WO | WO 1997047357 A1 | 12/1997 | |
| WO | 0234331 A2 | 5/2002 | |
| WO | WO 2002092165 A1 | 11/2002 | |
| WO | WO 2003005887 A2 | 1/2003 | |
| WO | WO 2003026735 A2 | 4/2003 | |
| WO | WO 2003092795 A1 | 11/2003 | |
| WO | WO 2004087116 A2 | 10/2004 | |
| WO | WO 2005002663 A2 | 1/2005 | |
| WO | WO 2005051306 A2 | 6/2005 | |
| WO | WO 2005065768 A1 | 7/2005 | |
| WO | WO 2005087307 A2 | 9/2005 | |
| WO | WO 2006138069 A1 | 12/2006 | |
| WO | WO 2007007058 A1 | 1/2007 | |
| WO | WO 2007012114 A1 | 2/2007 | |
| WO | 2007047852 A2 | 4/2007 | |
| WO | WO 2007047852 A2 | 4/2007 | |
| WO | WO 2007081764 A2 | 7/2007 | |
| WO | WO 2007107831 A2 | 9/2007 | |
| WO | WO 2008070807 A3 | 6/2008 | |
| WO | WO 2008075294 A1 | 6/2008 | |
| WO | WO 2008109862 A2 | 9/2008 | |
| WO | WO 2008121891 A1 | 10/2008 | |
| WO | WO 2009042217 A1 | 4/2009 | |
| WO | WO 2009111142 A2 | 9/2009 | |
| WO | WO 2010021977 A1 | 2/2010 | |
| WO | WO 2010055421 A1 | 5/2010 | |
| WO | WO 2010114998 A1 | 10/2010 | |
| WO | WO 2010124128 A1 | 10/2010 | |
| WO | WO 2011005607 A1 | 1/2011 | |
| WO | WO 2011136875 A1 | 11/2011 | |
| WO | WO 2012050200 A1 | 4/2012 | |
| WO | WO 2012075195 A1 | 6/2012 | |
| WO | WO 2012080964 A1 | 6/2012 | |
| WO | WO 2012/094346 A2 | 7/2012 | |
| WO | WO 2012100260 A2 | 7/2012 | |
| WO | WO 2012129574 A2 | 9/2012 | |
| WO | WO 2013071307 A1 | 5/2013 | |
| WO | WO 2013071309 A1 | 5/2013 | |
| WO | WO 2013152124 A1 | 10/2013 | |
| WO | WO 2013179230 A1 | 10/2013 | |
| WO | WO 2013188965 A1 | 12/2013 | |
| WO | WO 2014005075 A1 | 1/2014 | |
| WO | WO 2014031142 A1 | 2/2014 | |
| WO | WO 2014089299 A2 | 6/2014 | |
| WO | WO 2014144785 A1 | 9/2014 | |
| WO | WO 2014149895 A1 | 9/2014 | |
| WO | WO 2014205356 A2 | 12/2014 | |
| WO | WO 2014209877 A1 | 12/2014 | |
| WO | WO 2015000800 A1 | 1/2015 | |
| WO | WO 2015048563 A2 | 4/2015 | |
| WO | WO 2015063127 A1 | 5/2015 | |
| WO | WO 2015106286 A1 | 7/2015 | |
| WO | WO 2016029159 A2 | 2/2016 | |
| WO | WO 2016033369 A1 | 3/2016 | |
| WO | WO 2016033372 A1 | 3/2016 | |
| WO | WO 2016064761 A1 | 4/2016 | |
| WO | WO 2016110804 A1 | 7/2016 | |
| WO | WO 2016112398 A1 | 7/2016 | |
| WO | WO 2016172239 A1 | 10/2016 | |
| WO | WO 2017011410 A1 | 1/2017 | |
| WO | WO 2017024276 A1 | 2/2017 | |
| WO | WO 2017035512 A1 | 3/2017 | |
| WO | WO 2017044904 A1 | 3/2017 | |
| WO | WO 2017058913 A1 | 4/2017 | |
| WO | WO 2017062508 A1 | 4/2017 | |
| WO | WO 2017117450 A1 | 7/2017 | |
| WO | WO 2017146659 A1 | 8/2017 | |
| WO | WO 2018039296 A2 | 3/2018 | |
| WO | WO 2018106843 A1 | 6/2018 | |
| WO | WO 2018140531 A1 | 8/2018 | |
| WO | WO 2018217791 A1 | 11/2018 | |
| WO | WO 2019211314 A1 | 11/2019 | |
| WO | WO 2020041502 A1 | 2/2020 | |

(56) References Cited

FOREIGN PATENT DOCUMENTS

WO  WO 2020041633 A1  2/2020
WO  WO 2020236946 A1  11/2020

OTHER PUBLICATIONS

Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER '95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.
Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 20 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.

(56) References Cited

OTHER PUBLICATIONS

Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.
Extended European Search Report from European Patent Application No. 21185266.0, dated Feb. 11, 2022; 6 pages.
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.
Wenger, N. et al., "Closed-loop neuromodulation of spinal sensorimotor circuits controls refined locomotion after complete spinal cord injury," Science Translational Medicine, vol. 6, No. 255, Sep. 24, 2014, 10 pages.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 15 pages.
Ganty, D. et al., "A Lead for Neuromodulation," U.S. Appl. No. 15/989,598, filed May 25, 2018, 23 pages.
Abernethy, J. et al., "Competing in the Dark: An Efficient Algorithm for Bandit Linear Optimization", Conference on Learning Theory, (2008), 13 pages.
Anderson, K., "Targeting Recovery: Priorities of the Spinal Cord-Injured Population," Journal of Neurotrauma, vol. 21, No. 10, (Oct. 2004), 13 pages.
Angeli, C. et al., "Altering spinal cord excitability enables voluntary movements after chronic complete paralysis in humans," Brain, vol. 137, No. 5, May 2014, Available Online Apr. 8, 2014, 16 pages.
Auer, P. "Using Confidence Bounds for Exploitation-Exploration Trade-offs", Journal of Machine Learning Research, vol. 3, (2002), pp. 397-422.
Auer, P. et al., "Finite-time Analysis of the Multiarmed Bandit Problem", Machine Learning, vol. 47, No. 2, (2002), pp. 235-256.
Azimi, J. et al., "Batch Active Learning via Coordinated Matching", In Proceedings of the 29th International Conference on Machine Learning, (2012), 8 pages.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Brochu, E. et al., "A Tutorial on Bayesian Optimization of Expensive Cost Functions, with Application to Active User Modeling and Hierarchical Reinforcement Learning", In TR-2009-23, UBC, (2009), 49 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group Ia Synaptic Input to Fast and Slow Twitch Motor Units of Cat Triceps Surae", The Journal of Physiology, vol. 196, vol. 3, (Jun. 1, 1968), 26 pages.
Dani, V. et al., "Stochastic Linear Optimization Under Bandit Feedback", In Proceedings of the 21st Annual Conference on Learning Theory (COLT), (2008), 15 pages.
Danner, S. et al., "Human spinal locomotor control is based on flexibly organized burst generators," Brain, vol. 138, No. 3, (Mar. 2015), Available Online Jan. 12, 2015, 12 pages.
Danner, S. M. et al., "Body Position Influences Which neural structures are recruited by lumbar transcutaneous spinal cord stimulation", PLoS One, vol. 11, No. 1, (2016), 13 pages.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. M. et al., "Evidence for a Spinal Central Pattern Generator in Humans", Annals New York Academy Sciences, vol. 860, (1998), pp. 360-376.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Ganley, K. J. et al., "Epidural Spinal Cord Stimulation Improves Locomotor Performance in Low Asia C, Wheelchair-Dependent, Spinal Cord-Injured Individuals: Insights from Metabolic Response", Top. Spinal Cord Inj. Rehabil., vol. 11, No. 2, (2005), pp. 60-63.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-177.
Harrison, P. et al., "Individual Excitatory Post-Synaptic Potentials Due to Muscle Spindle Ia Afferents in Cat Triceps Surae Motoneurones," The Journal of Physiology, vol. 312, No. 1, (Mar. 1981), pp. 455-470.

(56) References Cited

OTHER PUBLICATIONS

Hennig, P. et al., "Entropy Search for Information-Efficient Global Optimization" Journal of Machine Learning Research (JMLR), vol. 13, (Jun. 2012), pp. 1809-1837.
Herman, R. et al., "Spinal cord stimulation facilitates functional walking in a chronic, incomplete spinal cord injured," Spinal Cord, vol. 40, No. 2, (2002), 4 pages.
Hines, M. L. et al., "The Neuron Simulation Environment," Neural Computation, vol. 9, No. 6, (Aug. 15, 1997), 26 pages.
Hofstoetter, U. S. et al., "Effects of transcutaneous spinal cord stimulation on voluntary locomotor activity in an incomplete spinal cord injured individual", Biomed. Tech., vol. 58 (Suppl. 1), (2013), 3 pages.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, (Nov. 2003), Published Online Jul. 9, 2003, 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.
Jones, D. R. et al., "Efficient Global Optimization of Expensive Black-Box Functions", Journal of Global Optimization, vol. 13, (1998), pp. 455-492.
Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.
Kleinberg, R. et al., "Multi-armed bandits in metric spaces", In STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, (Apr. 2009), 27 pages.
Krassioukov, A. et al., "A Systematic Review of the Management of Orthostatic Hypotension Following Spinal Cord Injury," Archives of Physical Medicine and Rehabilitation, vol. 90, No. 5, (May 2009), 22 pages.
Krause, A. et al. "Contextual Gaussian Process Bandit Optimization", In Advances in Neural Information Processing Systems (NIPS), (2011), 9 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Krause, A. et al., "Near-optimal Nonmyopic Value of Information in Graphical Models", In UAI, (2005), 8 pages.
Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.
Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.
Lizotte, D. et al., "Automatic gait optimization with Gaussian process regression", In IJCAI, (2007), pp. 944-949.
Lozano, A. et al., "Probing and Regulating Dysfunctional Circuits Using Deep Brain Stimulation," Neuron, vol. 77, No. 3, (Feb. 6, 2013), 19 pages.
McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.
Minassian, K. et al., "Mechanisms of rhythm generation of the human lumbar spinal cord in repose to tonic stimulation without and with step-related sensory feedback", Biomed Tech., vol. 58, (Suppl. 1), (2013), 3 pages.
Minassian, K. et al., "Neuromodulation of lower limb motor control in restorative neurology", Clinical Neurology and Neurosurgery, vol. 114, (2012), pp. 489-497.
Minassian, K. et al., "Peripheral and central afferent input to the lumbar cord", Biocybemetics and Biomedical Engineering, vol. 25, No. 3, (2005), pp. 11-29.
Minassian, K. et al., "Posterior root-muscle reflex", Second Congress International Society of Intraoperative Neurophysiology (ISIN), Dubrovnik, Croatia, (2009), pp. 77-80.
Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.
Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.
Minev, I. R. et al., "Electronic dura mater for long-term multimodal neural interfaces," Science Magazine, vol. 347, No. 6218, (Jan. 9, 2015), 64 pages.
Minoux, M., Accelerated greedy algorithms for maximizing submodular set functions. Optimization Techniques, LNCS, (1978), pp. 234-243.
Nandra, M. S. et al., "A parylene-based microelectrode array implant for spinal cord stimulation in rats", Conference Proceedings IEEE Eng. Med. Biol. Soc., (2011), pp. 1007-1010.
Nandra, M. S. et al., "A wireless microelectrode implant for spinal cord stimulation and recording in rats", Presentation Abstract, 2013.
Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.
Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.
Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.
Prochazka, A. et al., "Ensemble firing of muscle afferents recorded during normal locomotion in cats," The Journal of Physiology, vol. 507, No. 1, (Feb. 15, 1998), 12 pages.

(56) References Cited

OTHER PUBLICATIONS

Prochazka, A. et al., "Models of ensemble filing of muscle spindle afferents recorded during normal locomotion in cats," The Journal of Physiology, vol. 507, No. 1, (Feb. 15, 1998), 15 pages.

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

Rasmussen, C. E. et al., "Gaussian Processes for Machine Learning (gpml) Toolbox", The Journal of Machine Learning Research, vol. 11, (2010), pp. 3011-3015.

Rasmussen, C. E. et al., "Gaussian Processes for Machine Learning", The MIT Press, Cambridge, Massachusetts, (2006), 266 pages.

Rasmussen, C.E. "Gaussian Processes for Machine Learning", Machine Learning 2003, L.N.A.I. 3176, pp. 63-71 (2003).

Rattay, F. et al., "Epidural electrical stimulation of posterior structures of the human lumbosacral cord: 2. Quantitative analysis by computer modeling", Spinal Cord, vol. 38, (2000), pp. 473-489.

Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.

Robbins, H., "Some Aspects of the Sequential Design of Experiments", Bull. Amer. Math. Soc., vol. 58, (1952), pp. 527-535.

Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.

Ryzhov, I. O. et al., "The knowledge gradient algorithm for a general class of online learning problems", Operations Research, vol. 60, No. 1, (2012), pp. 180-195.

Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.

Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.

Srinivas, N. et al., "Gaussian process optimization in the bandit setting: No regret and experimental design", In Proceedings of the 27th International Conference on Machine Learning, (2010), 17 pages.

Stienen, A. H. A. et al., "Analysis of reflex modulation with a biologically realistic neural network," Journal of Computer Neuroscience, vol. 23, No. 3, Available Online May 15, 2007, (Dec. 2007),16 pages.

Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.

Tenne, Y. et al., "Computational Intelligence in Expensive Optimization Problems", vol. 2 of Adaptation, Learning, and Optimization, Springer, Berlin Heidelberg, (2010), pp. 131-162.

Van Den Brand, R. et al., "Restoring Voluntary Control of Locomotion after Paralyzing Spinal Cord Injury," Science Magazine, vol. 336, No. 6085, (Jun. 1, 2012), 5 pages.

Wan, D. et al., "Life-threatening outcomes associated with autonomic dysreflexia: A clinical review," Journal of Spinal Cord Medicine, vol. 37, No. 1, Jan. 2014, 9 pages.

Ward, A. R., "Electrical Stimulation Using Kilohertz-Frequency Alternating Current", Physical Therapy, vol. 89, Published online Dec. 18, 2008, (2009), pp. 181-190.

Wenger, N. et al., "Spatiotemporal neuromodulation therapies engaging muscle synergies improve motor control after spinal cord injury," Natural Medicine, vol. 22, No. 2, (Feb. 2016), Available Online Jan. 18, 2016, 33 pages.

Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.

Widmer, C. et al., Inferring latent task structure for multitask learning by multiple kernel learning, BMC Bioinformatics, vol. 11, (Suppl 8:S5), (2010), 8 pages.

Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.

Zhang, T. C. et al., "Mechanisms and models of spinal cord stimulation for the treatment of neuropathic pain," Brain Research, vol. 1569, Published Online May 4, 2014, (Jun. 20, 2014), 13 pages.

* cited by examiner

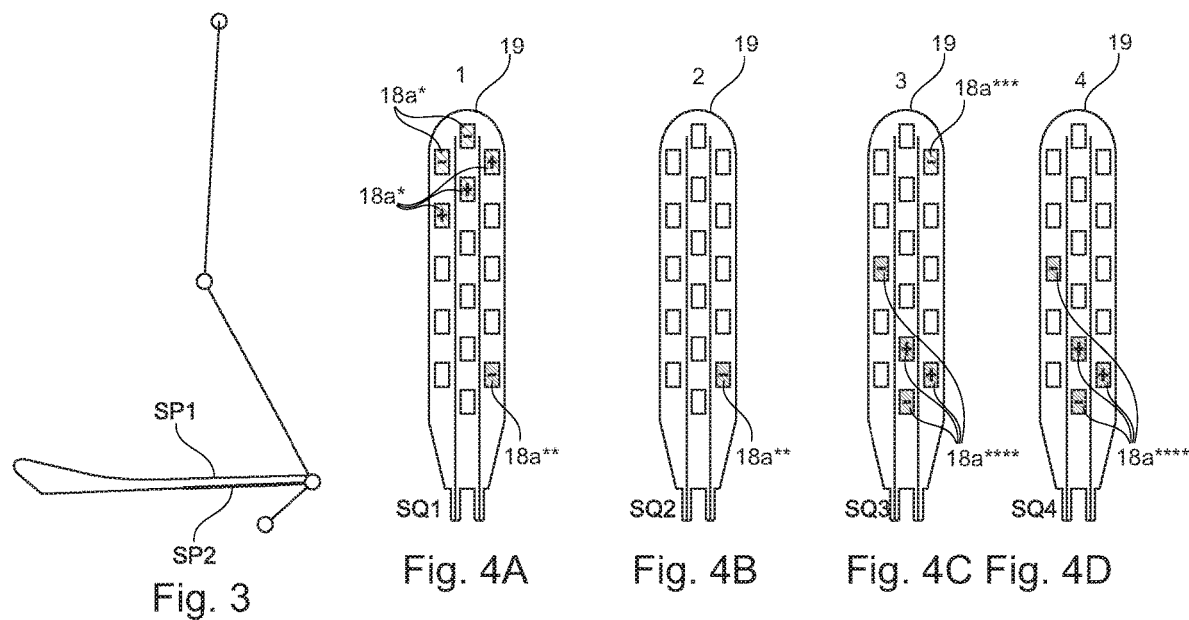

1-left ankle extension #2-left hip flexion #3-right ankle extention #4-right hip flexion #5-left knee extension

5-left knee extension    #6-right knee extension
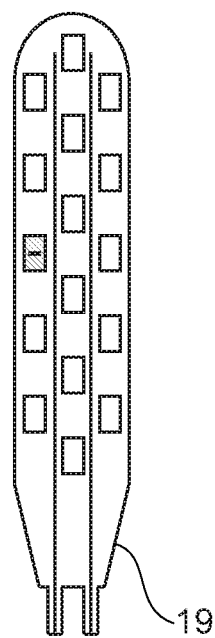
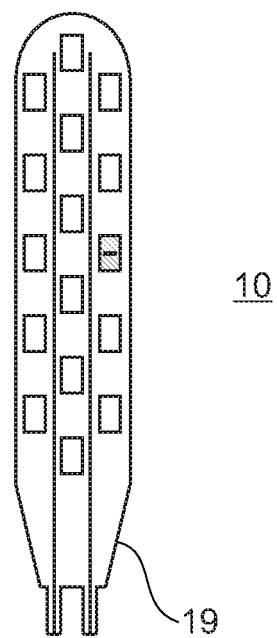
Fig. 11A
Fig. 11B

SYSTEM FOR NEUROMODULATION

CROSS REFERENCE TO RELATED APPLICATION

The present application is a continuation of U.S. Non-Provisional patent application Ser. No. 15/989,726, entitled "A SYSTEM FOR NEUROMODULATION", filed on May 25, 2018. The U.S. Non-Provisional Patent Application claims priority to European Patent Application No. 17178950.6-1666, entitled "A SYSTEM FOR NEUROMODULATION," filed on Jun. 30, 2017, the entire contents of which is incorporated herein by reference in its entirety for all purposes.

BACKGROUND AND SUMMARY

The present disclosure relates to a system for neuromodulation and/or neurostimulation, for the treatment of a subject. The system is in the field of improving recovery after neurological disorders such as spinal cord injury (SCI), and for example after disorders or injuries of the central nervous system.

EP 2 868 343 A1 discloses a system to deliver adaptive electrical spinal cord stimulation to facilitate and restore locomotion after neuromotor impairment. Inter alia, a closed-loop system for real-time control of epidural electrical stimulation is disclosed, comprising means for applying to a subject neuromodulation with adjustable stimulation parameters, means being operatively connected with a real-time monitoring component comprising sensors continuously acquiring feedback signals from subject, signals providing features of motion of a subject, the system being operatively connected with a signal processing device receiving feedback signals and operating real-time automatic control algorithms, and a signal processing device being operatively connected with the means and providing the means with new stimulation parameters with minimum delay. This known system improves consistency of walking in a subject with a neuromotor impairment. A Real Time Automatic Control Algorithm is used, comprising a feed-forward component employing a single input-single output model (SISO), or a multiple input-single output (MISO) model. Reference is also made to Wenger et al., Closed-loop neuromodulation of spinal sensorimotor circuits controls refined locomotion after complete spinal cord injury, in Science Translational Medicine, vol. 6, num. 255, 2014.

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

US 2002/0052539 A1 describes a partial closed loop, non-continuous and non-real-time emergency medical information communication system and corresponding methods. The system permits an emergency alert to be issued on the basis of information sensed or processed by an implantable medical device (IMD) implanted within a body of a patient. The IMD is capable of bidirectional communication with a communication module, a mobile telephone and/or a Personal Data Assistant (PDA) located outside the patient's body. The communication module, a mobile telephone or a PDA is capable of communicating an emergency alert generated by the IMD to a remote computer via a communication system. At the remote computer system it may be determined that emergency remedial action is required. If so, the action is executed remotely from the remote computer system in the IMD via the communication system.

Known stimulation systems use either Central Nerve System (CNS) stimulation, especially Epidural Electrical Stimulation (EES), or Peripheral Nerve System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (Capogrosso, M, et al., A Computational Model for Epidural Electrical Stimulation of Spinal Sensorimotor Circuits, Journal of Neuroscience 4 Dec. 2013, 33 (49) 19326-19340, Courtine et al., Transformation of nonfunctional spinal circuits into functional states after the loss of brain input, Nat Neurosci. 2009 October; 12(10): 1333-1342. Moraud et al, Mechanisms Underlying the Neuromodulation of Spinal Circuits for Correcting Gait and Balance Deficits after Spinal Cord Injury, Neuron Volume 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

Peripheral Nerve System (PNS) Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating, etc.).

It is an object of the present disclosure to improve a neuromodulation system, for example in the field of improving recovery after neurological disorders like spinal cord injury (SCI), for example after trauma or stroke or illness. Importantly, neuromodulation and/or neurostimulation may be provided in almost any environment and in daily life, may be adapted to a patient's needs and may provide the desired assistance in training and daily life for the patient, an may further be adjusted to the progress of the rehabilitation of the patient.

This object is solved according to the present disclosure by a system for neuromodulation and/or neurostimulation, for the treatment of a subject. Accordingly, a system for neuromodulation and/or neurostimulation, for the treatment of a subject is provided, comprising at least a stimulation controller, at least a stimulation pattern storage means, also referred to herein as a stimulation pattern storage drive, which is connected to the stimulation controller and which comprises stimulation data, at least an electrical stimulation device, at least an electrical interface between the electrical stimulation device and the subject, the electrical interface being connectable with at least a bio-interface of or with the nervous system of the subject, wherein the electrical interface and the bio-interface are arranged such that signals and/or data may be exchanged from the electrical interface to the bio-interface, or vice versa, wherein the stimulation data are pre-programmed patterns, which comprise at least a spatial component, which is related to a part of the nervous system being stimulated, a temporal component, which is related to a time at which each spatial component mentioned above is applied, and wherein the stimulation controller is capable to send configuration signals on the basis of the stimulation data to the electrical stimulation device such that via the electrical interface electrical stimulation may be provided to the bio-interface, wherein the electrical stimulation provided is characterized by stimulation parameters that vary over time in a pre-programmed manner.

The present disclosure is based on the basic idea that in the context of neuromodulation and/or neurostimulation, the electrical stimulation parameters defining the stimulation for the subject to be treated may vary cyclically over time in a pre-programmed manner, for example one cycle with pre-defined timings for the various stimulation patterns may be repeated over and over again. The use of pre-programmed temporal stimulation pattern data together with the use of pre-programmed spatial stimulation pattern data may allow a stimulation at a correct place at a correct time to facilitate, enable, or trigger an intended action of the subject. Such an action may be movement of extremities like feet and/or legs and/or arms, contraction and/or relaxation and/or any movement of muscles in connection with movement of the subject or cardiovascular functions of the subject (e.g. blood pressure control and/or blood circulation support and/or blood circulation control). Such an approach may be characterized as open-loop phasic stimulation. Basically, it may form a way to stimulate phasically the nervous system, for example the spinal cord of a subject or patient without the need for complex and/or complicated feedback systems. It may easily be implemented to promote locomotion, cyclical activity with physical training devices, and reduce orthostatic hypotension, after nervous system impairments such as spinal cord injury. Thus, it may be possible to improve a neuromodulation system, e.g. in the field of improving recovery after neurological disorders like spinal cord injury (SCI), for example after trauma or stroke or illness, in that neuromodulation and/or neurostimulation may be provided in almost any environment and in daily life, may be adapted to the patient's needs and may provide desired assistance in training and daily life for the patient, and may be further adjusted to the progress of the rehabilitation of the patient.

According to an embodiment of the system, the stimulation pattern storage means may comprise a spatial stimulation pattern data storage module for storing the spatial component, and the stimulation pattern storage means may comprise a temporal stimulation pattern data storage module for storing the temporal component, wherein the stimulation controller is capable to access the modules and/or to read out the modules independently from each other. This may allow easier and faster access to the different kinds of data and thus a faster process and stimulation may be possible. The link between the different kind of data may be established for example by meta data, such that the meta data form the link between the temporal component and the spatial component.

The stimulation pattern data may comprise data related to at least one of the parameters including stimulation frequency, stimulation amplitude, stimulation current, and/or pulse width. Generally speaking the stimulation pattern data may comprise data characterizing the stimulation to be applied.

Moreover, the electrical stimulation device may comprise a plurality of electrodes and the spatial component may comprise data related to the activation and non-activation of defined subsets of electrodes. By this, it may be possible to control and/or steer which part of the nervous system shall be stimulated. Subsets of electrodes may be defined as any value x out of the range 0 to n, n being the number of electrodes available. The plurality of electrodes may be arranged in an array, e.g. in an electrode array on a stimulation lead. Such a stimulation lead may be a lead paddle or a lead wire, or any kind of lead or carrier(s) having at least one lead or carrying at least a partial number of the electrodes.

The stimulation pattern data may comprise meta data, which may link the temporal component and spatial component to each other. This may allow faster access to the data and a faster and more efficient use of the stimulation pattern storage means. Also, a reprogramming may be simplified, as only additional or replacing meta data may have to be provided.

In an embodiment, the stimulation pattern data may comprise a sequence of stimulation patterns for a cyclic activity. As a cyclic activity in the broadest sense may be defined as a sequence of predefined movements, such sequence of movements may be assisted by a corresponding sequence of stimulation patterns provided by the system. In this way, rehabilitation of patients may be assisted and improved. Such a cyclic activity may be inter alia (but not limited to) a gait cycle, cycling, swimming, a rehabilitation activity and/or a training activity.

The sequences may comprise a plurality of ordered stages which may be arranged such that they form in their order a replication of physiological activation signals of relevant muscle groups at an appropriate time for a specific task or movement of the subject, the specific task or movement being at least one of walking, standing, standing up, sitting down, climbing staircases, cycling, lifting a foot, placing and/or moving an extremity, trunk, and/or head of the subject, and the like.

A stage being used in the context that an open-loop phasic stimulation program is a pre-defined sequence of stages that may activate several sets of active electrodes that in turn affect several muscle groups.

Thus, for specific movements specific matching sequences may be provided. Sequences may comprise a succession of well-timed sequences in order to replicate the activation of relevant muscle groups at an appropriate time as they would be for a specific task, the specific task being walking, standing, climbing staircase, cycling, etc.

The sequences may be part of an open-loop phasic stimulation. In this mode, electrode stimulation parameters may vary cyclically over time in a pre-programmed manner, i.e. one cycle with pre-defined timings for the various stimulation patterns (sites, frequency, amplitude, pulse width, etc.) may be repeated over and over again.

Such an open-loop phasic stimulation may be for example applied in the context of Epidural Electrical Stimulation (EES) with one or more implantable pulsegenerator(s) and epidural electrodes, which may be invasive and may be implanted in the spinal channel. The implantable pulse generator(s) and epidural electrodes (e.g. in the form of an electrode paddle with an array of electrodes) may be implanted minimally invasive or invasive. The epidural electrodes may be implanted in the vertebral channel through minimally-invasive or invasive surgical techniques. However, the system is not limited to such an application. Generally speaking, stimulation electrode arrays may also be non-invasive, e.g. by administering and providing transcutaneous stimulation to the spinal cord and/or other parts of the nervous system. Open-loop phasic stimulation may be also provided with external stimulators and invasive and/or non-invasive electrodes, such as in Functional Electrical Stimulation (FES) of individual muscles, Peripheral Nerve System (PNS) Stimulation of peripheral nerves and/or in transcutaneous spinal cord stimulation. It is also in general possible, that the afore-mentioned stimulation approaches may be combined.

Possible stimulation parameters for use in open-loop stimulation may be summarized as follows:

Frequency: 10-1000 Hz with preferred frequencies between 60 and 120 Hz.

Pulse Width: 100-1000 μs for implanted electrodes (invasive) and 200-2000 μs for surface electrodes (non-invasive and transcutaneous stimulation).

Amplitudes: 0.1-25 mA or 0.1-15 V for implanted electrodes (invasive) and 1-250 mA or 1-150 V for surface electrodes (non-invasive and transcutaneous stimulation).

Pulse shape: any type of charge-balanced pulse, either monophasic or bi-phasic.

Duration of each stage (i.e. stage being used in the context that an open-loop phasic stimulation program is a pre-defined sequence of stages that can activate several sets of active electrodes that in turn affect several muscle groups): 50-5000 ms.

Number of stages: approx. 1-10 (also other ranges possible, e.g. higher or lower then 10).

For example, the sequences for walking may comprise at least a first sequence related to left flexion and right extension, a second sequence related to right extension only, third sequence related to left extension and right flexion and a fourth sequence related to left extension only. Here, for example the first sequence related to left flexion and right extension may be approx. 400 ms, the second sequence related to right extension only may be approx. 600 ms, the third sequence related to left extension and right flexion may be approx. 400 ms and the fourth sequence related to left extension only may be also approx. 600 ms. Other suitable values may be chosen. In particular, the sequences related to extension only may be chosen with a longer duration than the sequence for flexion on one side and extension on the other side, e.g. approx. 1.5 times longer.

Furthermore, the stimulation pattern data may comprise a sequence of stimulation patterns exploiting a skeletal muscle pump for blood pumping from the extremities of the subject in the direction back to the heart of the subject. By this, it may be possible to assist the subject with blood pressure control and to avoid a blood pressure drop when the subject or patient wants to stand up, e.g. during rehabilitation for stretching in a standing frame in preparation to walk or generally for starting to walk or the like. Also, during walking such a stimulation may help the patient to perform his/her training.

The sequences may comprise at least a first sequence related to stimulation of a muscle in at least one extremity to contract the muscle and at least a second sequence related to stimulation of a muscle in this extremity to relax the muscle. The second sequence may have a lower stimulation or simply no stimulation may be provided. By this, a very simple but effective blood pumping may be realized.

In particular, the system may be an open-loop system. With such an open-loop system open-loop phasic stimulation may be provided.

In particular, open-loop may be understood as delivery of pre-programmed spatiotemporal stimulation or pre-programmed spatiotemporal stimulation patterns with spatial and temporal components.

The stimulation data for delivery of pre-programmed spatiotemporal stimulation or pre-programmed spatiotemporal stimulation patterns with spatial and temporal components may be pre-programmed patterns, which may comprise at least a spatial component, which is related to the part of the nervous system being stimulated a temporal component, which is related to the time at which each spatial component mentioned above is applied.

In contrast to closed-loop systems, open-loop may be understood such that neuromodulation and/or neurostimulation is provided, but feedback from the patient is not used or does not influence the stimulation data. Also, the stimulation provided by the stimulation device, inter alia the sequences provided, may be maintained. Under these unchanged stimulation sequences, when stimulation is applied to afferent sensory neurons prior to entering into the spinal cord or in the periphery, the patient may still influence—to some degree—an extent of a generated motor output by contributing more or less volitionally. Likely, stimulation-induced inputs to the spinal cord and volitional descending activity may be integrated at pre-motoneuronal and motoneuronal levels in the spinal cord and hence may influence each other and the amount of motor activity generated. As a consequence, the patient may, with unchanged stimulation frequencies, amplitudes, or pulse-widths within the pre-defined sequences of stimulation, exaggerate or suppress the generated motor outputs—to some degree—by contributing more or less volitionally. In any case, this may allow a simplified and reliable system. Also, the system may be less complex. It may form an additional system and/or supplement for existing systems or other systems.

For example, it may be possible that the system comprises and/or is connected and/or is connectable with a closed-loop system for neuromodulation and/or neurostimulation. Thus, a closed-loop and open-loop system may be provided and established. This may allow the use of the open-loop approach for specific, predefined tasks, whereas the closed-loop approach may be used for other tasks, where the closed-loop approach may promise more effect. A broader range of stimulation capabilities may be provided by such a combination.

The closed-loop system may work in real-time or may be—in other words—a real-time system such that feedback data being sensed by the system are processed as input variables for control of the system, and that this processing is done in real-time.

Real-time may be understood as real-time or close to real-time. Inter alia, a time frame and short delay between 0.0 to approximately 30 ms may be understood to fulfill the condition of real-time.

Furthermore, the system may be configured such that the stimulation data may be re-configured and/or adjusted on the basis of data being delivered by the closed-loop system, especially wherein the re-configuration and/or adjustment is done in real-time. There may be a real-time configuration of the pre-programmed stimulation pattern. In particular, the closed-loop system and its data may be used to adapt the stimulation data of the open-loop system. Such closed-loop system data may be delivered to the stimulation controller, which then may modify the stimulation data. In other words, the closed-loop system may be used to re-configure and/or adjust the stimulation data of the open-loop system.

The spatial component and the temporal component may be, as one example, configured by using the closed-loop system (or a closed-loop system), based for example on movement feedback on a cycle to cycle basis (e.g. as opposed to triggering events).

Also, the sequence of stimulation patterns may comprise at least one starting sequence. For example, the starting sequence may be for starting a cyclic activity (cf. above), like a gait cycle or the like, facilitated and/or induced by the feedback-controlled closed-loop phasic stimulation system as described above. It has been observed that maintaining an existing movement or sequence of movements is easier to maintain than to start it. Surprisingly, it has been found that even with a well-adjusted sequence of stimulation patterns, e.g. for a gait cycle, the patient to be treated has to try hard to start the gait cycle and the specific movement. By providing a starting sequence, which triggers the start of the gait cycle and the specific movements, better assistance for the patient may be provided. The starting sequence for starting the gait cycle is for example applied only at the beginning of a training sequence of the gait cycle, then followed by an iteratively applied sequence of stimulation patterns for the gait cycle. This kind of paradigm is, however, not limited to training or rehabilitation scenarios, but may also be used in daily life for assistance of users of such a system in order to enhance the movement capabilities of such patients and to increase their independence from care-giving.

It may be possible that the system may comprise an initialization module and initialization data, the initialization data being specific stimulation data being stored in the stimulation pattern storage means, wherein the initialization module is configured and arranged to control the electrical stimulation device based on the initialization data such that electrical stimulation device provides neuromodulation signals and/or neurostimulation signals, for an initialization action or movement of the subject. With such an initialization capability, the start of a specific movement or task may be facilitated. In particular, specific tasks like walking, standing, standing up, sitting down, climbing staircases, cycling, lifting a foot, placing and/or moving an extremity or the head of the subject and the like may be started, and after this initialization, supported by the system itself with open-loop phasic stimulation (or the stimulation is done by another system).

For example, the system may be configured and arranged such that the initialization module and initialization data are used to start the closed-loop system. It has been found that open-loop stimulation may be very beneficial and effective to "start-up" the task and to provide and trigger the start of the task, whereas during the task closed-loop stimulation may be provided.

Also, the system may comprise a fallback module and fallback module data, the fallback module data being specific stimulation data being stored in the stimulation pattern storage means, wherein the fallback module may be configured and arranged to control the electrical stimulation device based on the fallback module data such that electrical stimulation device provides neuromodulation signals and/or neurostimulation signals, for actions or movement of the subject, when the closed-loop system is unintentionally out of service. By this, the overall safety of a closed-loop system may be increased and enhanced. In such a case, the system itself has the capability to provide open-loop stimulation and closed-loop stimulation or the system is combined with a closed-loop system. As open-loop stimulation does not require any real-time information from the leg movement and positions of the patient, such an approach may be advantageous to maintain and provide at least basic stimulation capabilities, when closed-loop stimulation is temporarily not working (e.g., temporarily fails to detect or decode specific gait events otherwise triggering specific stimulation sequences).

In particular, it is possible that the fallback module data are neurostimulation signals, for actions or movement of the subject, when the closed-loop system for said subject being connected with the system is unintentionally out of service. Thus, a fallback functionality for the closed-loop system may be provided. Even with a system failure of the closed-loop system it may still be possible to provide open-loop phasic stimulation. Thus, for example in a scenario for stimulation of the legs, a patient may still be able even in case of a system failure of the open-loop system to reach his/her wheelchair, or simply continue with moving. This may also provide enough time for allowing the closed-loop system to restart.

Combinations of an open-loop system as defined above in connection with a closed-loop system maybe also called "hybrid systems".

As described above, in such hybrid systems open-loop stimulation and closed-loop stimulation may assist each other or form a combined open-loop and closed-loop stimulation system. Thereby, it may be allowed to have open-loop stimulation and closed-loop stimulation at the same time, e.g. to allow and trigger additional movements by means of open-loop stimulation during walking assisted by closed-loop stimulation. In this context possibilities are not restricted to this example and other examples are possible.

Also, such hybrid system may comprise—additionally or alternatively—a fallback solution, in particular open-loop stimulation as fallback for closed-loop stimulation.

The hybrid system approach may also be used to form an enhanced stimulation system with easier system initialization by means of assisting movement initialization with open-loop phasic stimulation, in particular as described above in connection with the initialization module and the initialization data and the starting sequence.

Furthermore a method for neuromodulation and/or neurostimulation, for the treatment of a subject, is explicitly disclosed. Accordingly, a method for neuromodulation and/or neurostimulation, for the treatment of a subject is provided, wherein the method may be performed by using at least an electrical stimulation device and at least an electrical interface between the stimulation device and the subject, and at least a subject neural interface, being connected to the electrical interface, wherein the subject may be stimulated with the electrical stimulation device by using stimulation pattern data and wherein the stimulation data are pre-programmed patterns, which comprise at least a spatial component, which may be related to the part of the nervous system being stimulated a temporal component, which may be related to the time at which each spatial component mentioned above is applied and wherein on the basis of the stimulation pattern data the electrical stimulation device provides via the electrical interface electrical stimulation to the subject neural interface, wherein the electrical stimulation provided may be characterized by stimulation parameters that vary over time in a pre-programmed manner.

Furthermore, the method may be performed by using the system for neuromodulation and/or neurostimulation as specified above.

Also, it may be possible that the electrical stimulation may be provided in sequences and/or cyclically and/or repeatedly.

Additionally, the electrical stimulation may be provided in sequences which comprise a plurality of ordered sequences which are arranged such that they form in their order a replication of the physiological activation signals of relevant muscle groups at an appropriate time for a specific task or movement of the subject, the specific task or movement being at least one of walking, standing, standing up, sitting down, climbing staircases, cycling, lifting a foot, placing and/or moving an extremity or the head of the subject, and the like.

As an example, for walking that the electrical stimulation may address in the legs and feet of the subject at least in a first step left flexion and right extension, in a second step right extension only, in a third step left extension and right flexion, in a fourth step left extension only.

It may also be possible that the electrical stimulation stimulates muscles of the subject for blood pumping from the extremities of the subject in the direction back to the heart of the subject, for example wherein at least one muscle is stimulated such that the muscle contracts and relaxes alternately.

BRIEF DESCRIPTION OF THE FIGURES

Further details and advantages of the present disclosure shall now be disclosed in connection with the drawings.

FIG. 3 shows a schematic diagram of the leg and feet trajectory.

FIGS. 4A-D show a schematic view of an electrode paddle of the system with specifically activated electrodes for a gait cycle stimulation.

FIGS. 11A-B show a schematic view of an electrode paddle of the system with specifically activated electrodes for knee extension stimulation to facilitate sit-to-stand scenarios.

DETAILED DESCRIPTION

Figure 1:
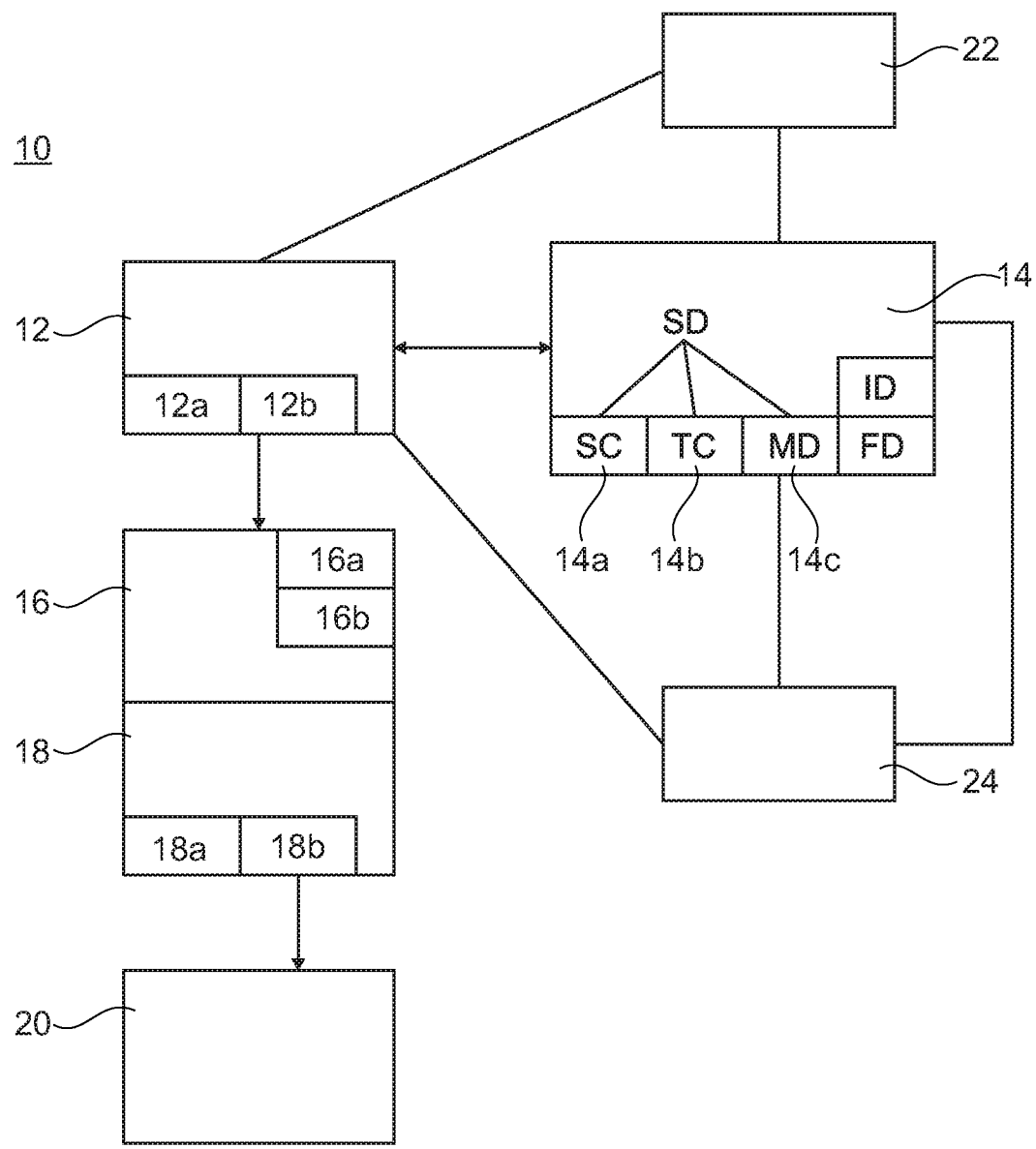
FIG. 1 shows a schematic view of the layout of an embodiment according to the present disclosure of the neuromodulation and/or neurostimulation system.

FIG. 1 shows in a schematic view the layout of the neuromodulation and/or neurostimulation system 10 according to the present disclosure.

The system 10 is a system for improving recovery after neurological disorders such as spinal cord injury (SCI), for example after disorders or injuries of the central nervous system.

The system 10 as shown is an open-loop phasic stimulation system 10.

The system 10 comprises a controller 12.

The controller 12 comprises also an input means 12a, which is configured and arranged to provide the controller 12 with additional input signals.

Such input signals may be alternative and/or additional stimulation data, which are provided to and installed on the system 10.

Moreover, the controller 12 comprises an interface 12b, which is configured and arranged to connect the controller 12 with other systems (not shown). Such system may be, inter alia and not limited to, e.g. another closed-loop system for neuromodulation and/or neurostimulation for the treatment of a patient.

Furthermore, there is a stimulation pattern storage means 14.

In the stimulation pattern storage means 14 stimulation data SD are stored and available for the system 10.

The stimulation data SD comprise data related to at least one of the parameters stimulation frequency and/or stimulation amplitude and/or stimulation current and/or pulse width or the like or other suitable parameters, either direct parameters or indirect relevant parameters. Generally speaking the stimulation data may comprise data characterizing the stimulation to be applied.

The stimulation data SD comprise pre-programmed patterns, which comprise at least a spatial component SC, which is related to the part of the nervous system being stimulated a temporal component TC, which is related to the time at which each spatial component mentioned above is applied.

The stimulation pattern storage means 14 has a spatial stimulation pattern data storage module 14a for the spatial component and a temporal stimulation pattern data storage module 14b for the temporal component.

The stimulation pattern storage means 14 also has a meta data storage module 14c for storing meta data MD.

The meta data MD link the temporal component and spatial to each other.

Furthermore, there is an electrical stimulation device 16. The stimulation device 16 comprises the necessary electronics like a pulse generator 16a and/or an interface 16b being connectable to a pulse generator.

The pulse generator may be an Implantable Pulse Generator (IPG) or an external or non-implantable pulse generator.

There is an electrical interface 18 of the system 10.

The interface 18 may be formed by or comprise one or more electrodes 18a, 18b.

Here, the electrodes 18a may be implanted or implantable electrodes and the electrodes 18b may be electrodes for providing stimulation non-invasively and transcutaneously.

The electrodes 18a are preferably arranged in an electrode array. It is possible that the electrodes 18a are part of an electrode paddle (e.g. 19) for spinal cord stimulation.

The spatial component SC comprises data related to the activation and non-activation of defined subsets of electrodes 18a, 18b. Also, these data may comprise the information as to whether the electrode is activated as cathode or anode. By this, it may be possible to control and/or steer the exact site of the nervous system that shall be stimulated. Subsets of electrodes may be defined as any value x out of the range 0 to n, n being the number of electrodes available.

The interface 18 is in contact with a bio-interface 20 of the subject to be treated with the system 10. There can be several bio-interfaces 20.

As further shown in FIG. 1, the system 10 comprises an initialization module 22.

In the stimulation pattern storage means 14 initialization data ID are stored and made available for the system 10.

The initialization data ID are specific stimulation data being stored in the stimulation pattern storage means 14. It is also possible to store the initialization data ID directly in the initialization module 22.

The initialization module 22 is configured and arranged to control the electrical stimulation device 16 via the controller 12 based on the initialization data ID such that the electrical stimulation device 16 provides neuromodulation signals and/or neurostimulation signals, for an initialization action or movement of the subject.

As a special functionality, the system 10 may be configured and arranged such that the initialization module 22 and initialization data ID are used to start a closed-loop system. For this, e.g. the interface 12b may be used.

Also, the system 10 comprises a fallback module 24.

In the stimulation pattern storage means 14 fallback module data FD are stored and made available for the system 10.

The fallback module data FD are specific stimulation data being stored in the stimulation pattern storage means 14. It is also possible to store the fallback module data FD directly in the fallback module 24.

The fallback module 24 is configured and arranged to control the electrical stimulation device 16 via the controller 12 based on the fallback module data FD such that electrical stimulation device 16 provides neuromodulation signals and/or neurostimulation signals, for actions or movement of the subject, when the closed-loop system is unintentionally out of service.

The components of the system 10 are linked as follows:

The controller 12 is connected with the stimulation pattern storage means 14, the electrical stimulation device 16, the initialization module 22, and the fallback module 24.

The stimulation device 16 is in connection with the interface 18, i.e. with the electrodes 18a and 18b. Thus, the stimulation device 16 may provide stimulation via the interface 18, i.e. via the electrodes 18a and 18b.

In operation, the electrical interface 18 is connected with the bio-interface 20 of or with the nervous system of the subject, wherein the electrical interface 18 and the bio-interface 20 are arranged such that signals and/or data may be exchanged from the electrical interface 18 to the bio-interface 20.

It may be possible that in cases with combinations of open-loop and closed-loop, the data exchange between the electrical interface 18 and the bio-interface 20 may be also vice versa.

Such a data exchange may be established via input means 12a and interface 12b.

The stimulation controller 12 is capable to access the spatial stimulation pattern data storage module 14a and the temporal stimulation pattern data storage module 14b and to access and read out the modules independently from each other.

This may allow easier and faster access to the different kind(s) of data and thus a faster process and stimulation may be provided by the system 10.

The link between the different kind(s) of data is established by means of the meta data MD stored in the meta data storage module 14c, such that the meta data MD form the link between spatial component SC and temporal component TC.

So, the stimulation pattern storage means 14 provides storage capacity for data, inter alia control instructions for performing the control of the system 10 by means of the controller 12, which is capable to control the overall system based on the instructions stored in the stimulation pattern storage means 14.

Such instructions include but are not limited to stimulation sequences as follows:

Inter alia, in the shown embodiment the stimulation data SD comprise a sequence of stimulation patterns for a gait cycle, i.e. a predefined sequence of stimulation of specific sites of the CNS and/or PNS for recruiting muscle groups to facilitate movements.

Also, the sequence of stimulation patterns for a gait cycle may comprise at least one starting sequence for starting the gait cycle.

Then, the sequences comprise a plurality of ordered sequences which are arranged such that they form in their order a replication of the physiological activation signals or signal pattern of relevant muscle groups at the appropriate time for a specific task or movement of the subject, the specific task or movement being at least one of walking, standing, standing up, sitting down, climbing staircases, cycling, lifting a foot, placing and/or moving an extremity or stabilizing the trunk of the subject and the like.

Thus, for specific movements specific matching sequences may be provided. Sequences may comprise a succession of well-time sequences in order to replicate the activation of relevant muscle groups at an appropriate time as they would be for a specific task, the specific task being walking, standing, climbing staircase, cycling, etc.

The sequences may be part of an open-loop phasic stimulation. In this mode, electrode stimulation parameters may vary cyclically over time in a pre-programmed manner, i.e. one cycle with pre-defined timings for the various stimulation patterns (sites, frequency, amplitude, pulse width, etc.) may be repeated over and over again.

The function of the system 10 e.g. during a treatment and/or neurorehabilitation training of a patient may be described as follows.

The system 10 provides open-loop phasic stimulation.

In this mode, electrode stimulation parameters vary cyclically over time in a pre-programmed manner, i.e. one cycle with pre-defined timings for the various stimulation patterns (sites, frequency, amplitude, pulse width, etc.) is repeated over and over again.

The system 10 provides open-loop phasic stimulation in the context of Epidural Electrical Stimulation (EES) with one implantable pulse generator(s) and an epidural electrode array on an electrode paddle (cf. also FIGS. 4A-4D), which is implanted in the epidural space.

However, the system is not limited to such an application. It may consist of several epidural electrode arrays arranged over the lumbar, thoracic, and cervical spinal cord (and connected to more than one implantable pulse generator) for the control of lower extremity, trunk, and upper extremity function, respectively. Generally speaking, stimulation electrode arrays may also be non-invasive, e.g. by administering and providing transcutaneous stimulation to the spinal cord and/or other parts of the nervous system. Open-loop phasic stimulation may be also provided with external stimulators and invasive and/or non-invasive electrodes, such as in Functional Electrical Stimulation (FES) of individual muscles, Peripheral Nerve System (PNS) Stimulation of peripheral nerves and/or in transcutaneous spinal cord stimulation. It is also in general possible, that the aforementioned stimulation approaches may be combined.

The stimulation parameters for use this open-loop stimulation are chosen from the following ranges:

Frequency: 10-1000 Hz with preferred frequencies between 60 and 120 Hz.

Pulse Width: 100-1000 µs for implanted electrodes (invasive) and 200-2000 µs for surface electrodes (non-invasive and transcutaneous stimulation).

Amplitudes: 0.1-25 mA or 0.1-15 V for implanted for implanted electrodes (invasive) and 1-250 mA or 1-150 V for surface electrodes (non-invasive and transcutaneous stimulation).

Pulse shape: any type of charge-balanced pulse, either monophasic or bi-phasic.

Duration of each stage (i.e. stage being used in the context that an open-loop phasic stimulation program is a pre-defined sequence of stages that can activate several sets of active electrodes that in turn affect several muscle groups): 50-5000 ms.

Number of stages: approx. 1-10 or selected in the range of between approx. 1-100.

Figure 2:
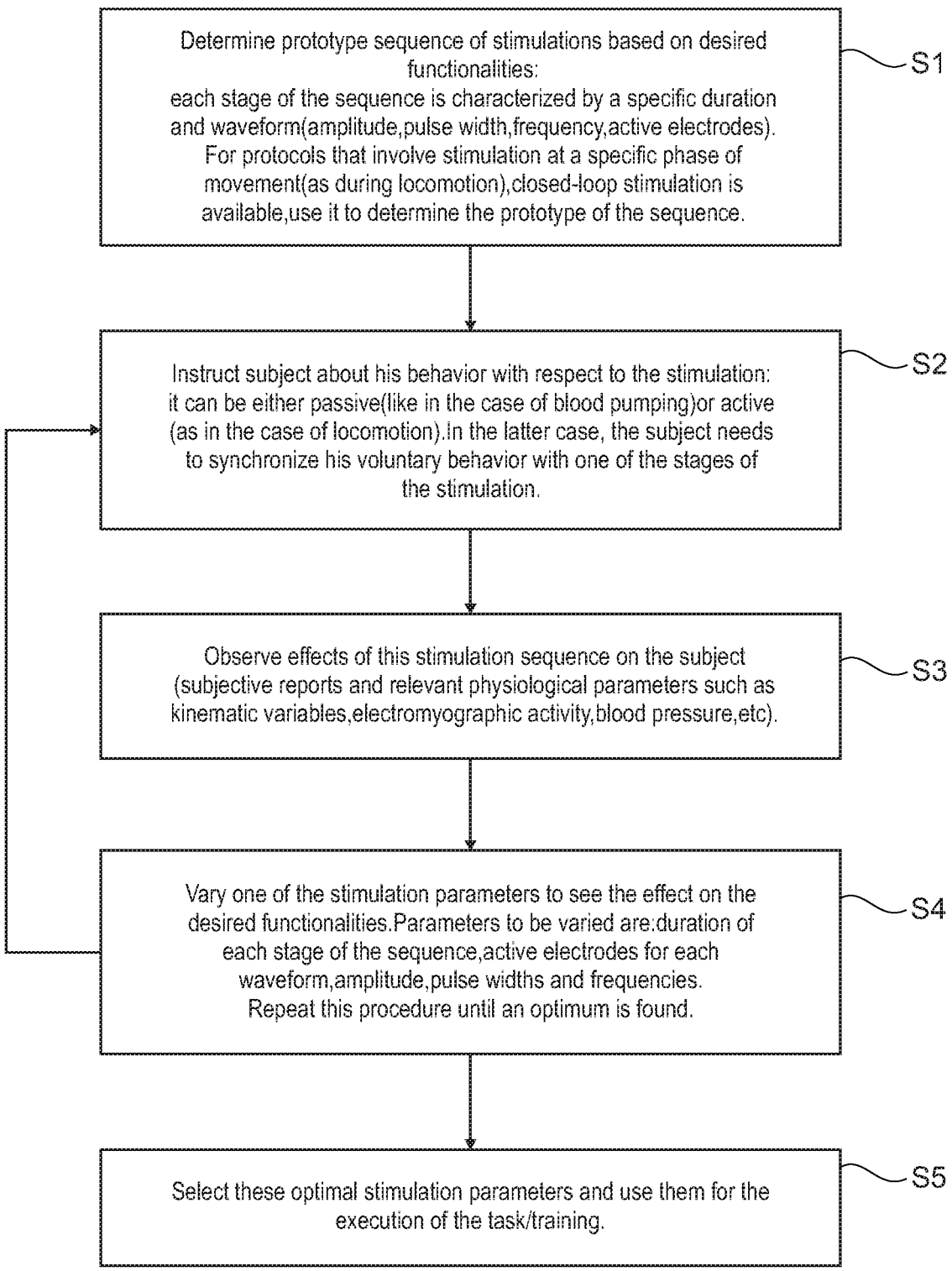
FIG. 2 shows an example workflow diagram of the system of FIG. 1.

FIG. 2 shows an example workflow of the system 10 for setting up an open-loop stimulation.

In step S1 a prototype sequence of stimulation based on desired functionalities is determined.

Here, each stage (i.e. stage being used in the context that an open-loop phasic stimulation program is a pre-defined sequence of stages that may activate several sets of active electrodes that in turn may affect several muscle groups) of the sequence is characterized by a specific duration and waveform (amplitude, pulse width, frequency of active electrodes). For protocols that involve stimulation at a specific phase of movement (as during locomotion), availability of closed-loop stimulation may facilitate determining the prototype of the sequence.

In step S2 the subject (patient) is instructed about his behavior with respect to the stimulation.

Here, it may be either passive (like in the case of blood pumping) or active (as in the case of locomotion). In the latter case, the subject may synchronize his voluntary behavior with the stages of the stimulation.

Generally speaking, the subject may synchronize his voluntary contributions to all stages of the stimulation, but typically they initiate a movement by concentrating on a single stage, e.g., left hip flexion. Then, to continue the rhythmic movement, the subject may synchronize to all stages in the sequence they appear.

In step S3 the effects of this stimulation sequence are observed.

Here, the observed effects of this stimulation sequence on the subject, i.e. inter alia subjective reports (interaction between patient and training personnel and physician) and relevant physiological parameters such as kinematic variables, electromyographic (EMG) activity, blood pressure, electroencephalography (EEG) and the like are reviewed.

In step S4 one of the stimulation parameters is varied to see the effect on the desired functionalities.

Parameters to be varied are duration of each stage of the sequence, active electrodes for each waveform, amplitudes, pulse widths and frequencies. This procedure may be repeated and iterated until an optimum is found.

In step S5 the optimal stimulation parameters are selected and used for the execution of the task or training.

For example, the sequences for walking comprise at least a first sequence related to left flexion and right extension, a second sequence related to right extension only, third sequence related to left extension and right flexion and a fourth sequence related to left extension only.

FIG. 3 shows a schematic diagram of one leg and foot trajectory during locomotion enabled by phasic stimulation as specified above in connection with the sequences for walking, with two patterns of stimulation applied sequentially, one during the swing phase SP1 and one during the stance phase SP2 of the gait.

FIGS. 4A-D show the corresponding activation of the electrodes 18a on an electrode paddle 19.

In this example, the first sequence SQ1 (FIG. 4A) related to left flexion and right extension is 400 ms, the second sequence SQ2 (FIG. 4B) related to right extension is 600 ms, the third sequence SQ3 (FIG. 4C) related to left extension and right flexion is 400 ms and the fourth sequence SQ4 (FIG. 4D) related to left extension only is 600 ms.

The electrode configurations corresponding to the sequences SQ1 to SQ4 indicated above are further discussed below.

In FIG. 4A activated electrodes 18a* relate to the stimulation of the left leg for left flexion.

In FIG. 4A and FIG. 4B activated electrodes 18a** relate to the stimulation of the right leg for right extension.

In FIG. 4C activated electrode(s) 18a*** relate to the stimulation of the right leg for right flexion.

In FIG. 4C and FIG. 4D activated electrode(s) 18a**** relate to the stimulation of the left leg for left extension.

The resulting stimulation patterns, which are the result of the specific electrodes 18a on the electrode paddle 19 shown in FIGS. 4A-D, are for promoting respectively flexion and extension of either the left or the right leg.

In this specific example, the right extension and right flexion electrodes are 'mono-polar' selections and the active site of the IPG is set as the return electrode.

Figure 5:
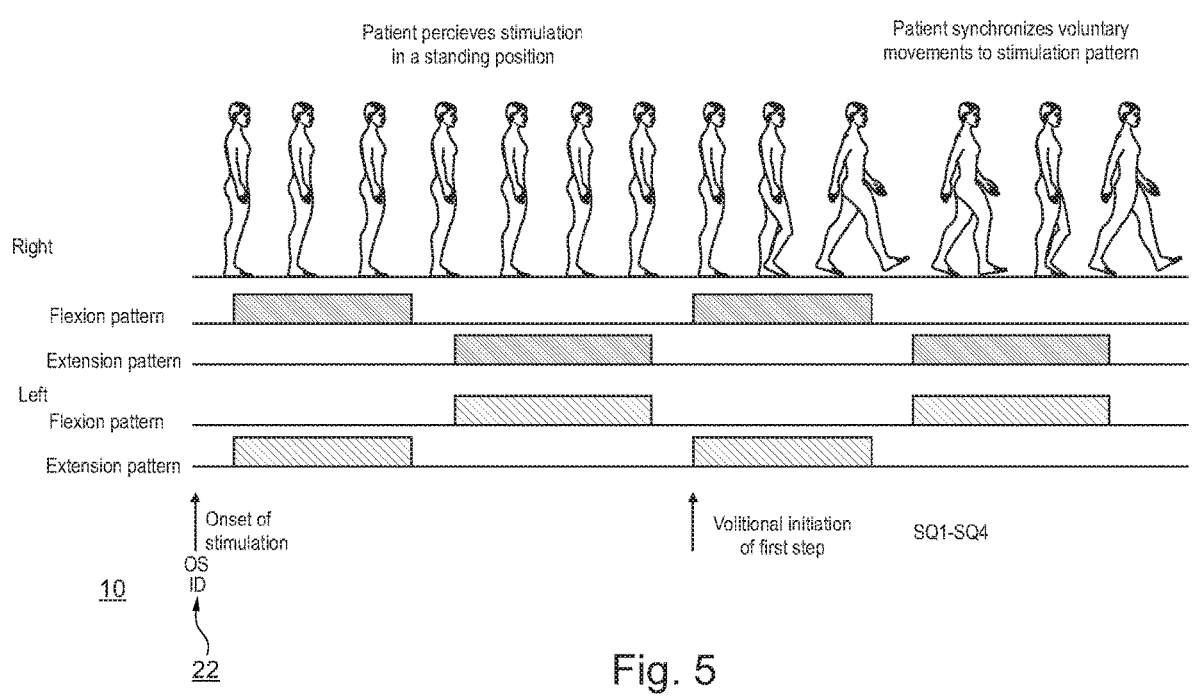
FIG. 5 shows a schematic overview of the concept of open-loop phasic stimulation for walking.

FIG. 5 shows the concept and overview of open-loop phasic stimulation for walking.

As shown in FIG. 5, there is an Onset of Stimulation OS. This Onset of Stimulation OS is done by means of the initialization module 22 and the initialization data ID.

Here, the initialization module 22 controls the electrical stimulation device 16 via the controller 12 based on the initialization data ID such that the electrical stimulation device 16 provides neuromodulation signals and/or neurostimulation signals, for an initialization action or movement of the subject to do the Onset of Stimulation OS (cf. also FIG. 1).

With the volitional initiation of the first step VI the sequences SQ1 to SQ4 are provided as described above.

Figure 6A:
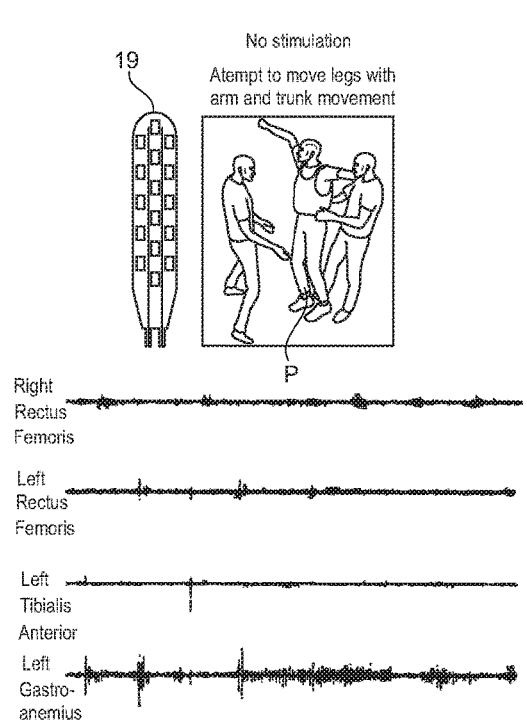
FIGS. 6A-B show a schematic overview of the training of a patient without and with open-loop phasic stimulation by using the system as shown in FIG. 1.
Figure 6B:
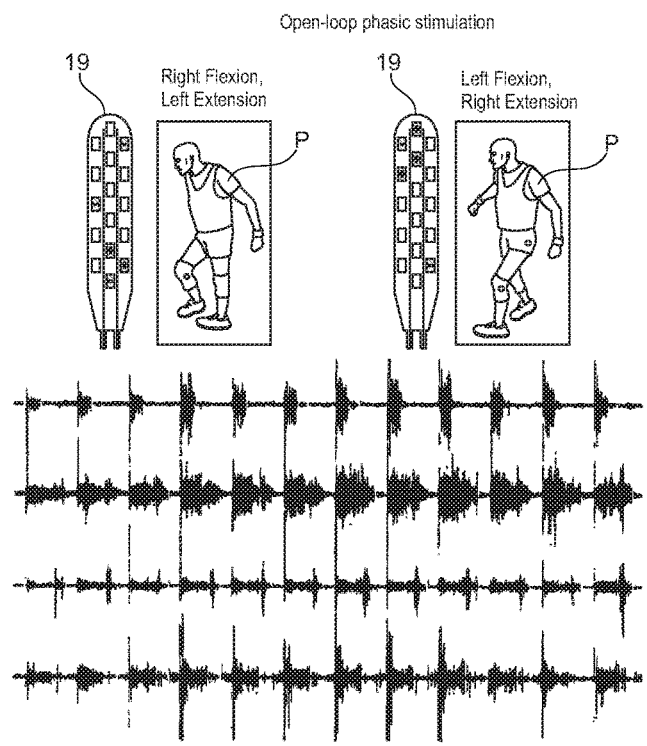

FIG. 6A and FIG. 6B show the difference between absence and presence of open-loop phasic stimulation in connection with the training of a patient P by using the system as shown in FIG. 1. Exemplary patient P has a chronic incomplete SCI, with his left leg completely paralyzed and with some residual function in his right leg.

In both cases shown in FIG. 6A and FIG. 6B, the patient is placed in a robotic system supporting 35% of his body weight.

In these conditions and in the absence of open-loop EES (FIG. 6A, left), the patient is unable to initiate a single step and instead attempts to move his legs using his trunk and arm movements. Leg muscles show almost no EMG activity during this attempted movement.

By contrast, the application of open-loop EES (FIG. 6B, right) enables the patient to perform more than 10 consecutive steps with minimal assistance at the hips, showing the natural alternation of left and right stance and swing phases, accompanied by strong rhythmical EMG activity in all recorded leg muscles.

This shows that open-loop phasic stimulation by using EES enables locomotion and generates EMG activity in a person with incomplete spinal cord injury.

The above can be summarized in other words as follows:

Locomotion is accomplished via the cyclical coordinated alternation of flexion and extension muscle synergies at specific phases of the gait cycle. Open-loop phasic stimulation defines a sequence of pre-programmed stimulation patterns that promote movements at each phase of the gait cycle. Typically, the flexion phase on one leg coincides with the extension phase on the contralateral leg. An example of open-loop phasic stimulation program for locomotion is shown in FIG. 3 and FIG. 4A-D.

In order to use the stimulation for walking, the patient has to synchronize his attempts to move his leg with the timing of the stimulation (FIG. 5). It is important to understand that the stimulation does not move the legs without voluntary inputs from the brain of the patient. First, the patient feels the onset of the stimulation discharges in standing position, and then tries to initiate his gait with the appropriate timing. It has been observed that that patients may easily adjust to this type of stimulation and use it effectively for walking.

Open-loop phasic stimulation as provided by the system 10 may be also used for any cyclical activity on physical training devices (bike, elliptical device, rowing machine):

Using the same principle, open-loop phasic stimulation programs may be implemented to promote cyclical coordinated leg muscle activity for any type of cyclical training activity, such as biking, walking on an elliptical device or using a rowing machine. Depending on the context, not all available stimulation patterns need to be used. For example, biking in reclined position requires mostly extension stimulations rather than flexion. In that case, extension stimulations alternate between the left and right leg at a fixed rhythm, for example.

Further stimulation patterns are shown in FIGS. 7A-B to FIGS. 11A-B.

Activated electrodes 18a of the electrode paddle 19 have the reference number 18a*.

Figure 7A:
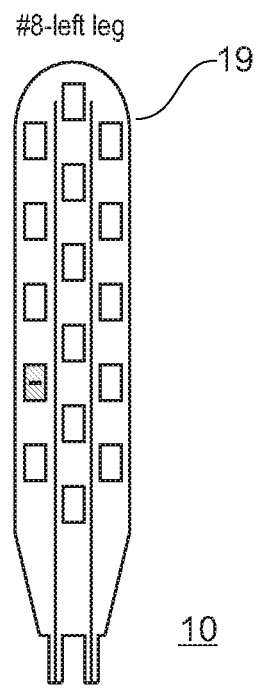
FIGS. 7A-B show a schematic view of an electrode paddle of the system with specifically activated electrodes for left leg stimulation.

FIG. 7A shows a schematic view of the electrode paddle 19 of the system 10 with specifically activated electrodes for left leg stimulation. Such kind of stimulation may be used to train specifically one leg, here the left leg.

Figure 7B:
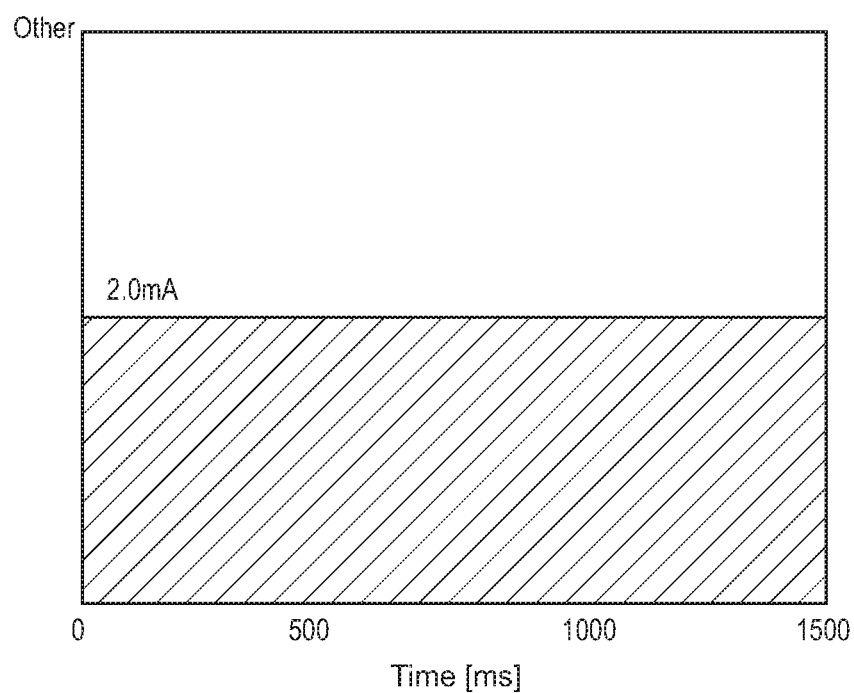

As can be derived from FIG. 7B, specific left leg stimulation is done for with a current of 2.0 mA for 1500 ms.

Figure 8A:
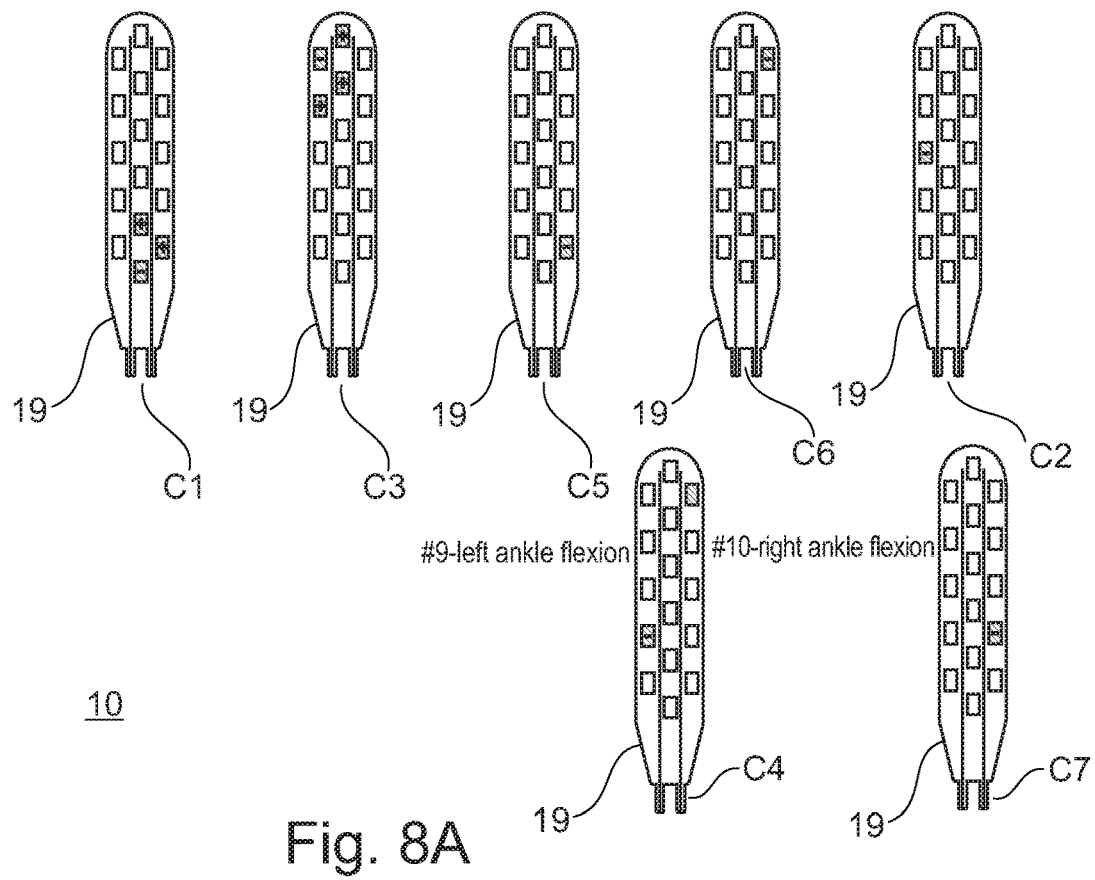
FIGS. 8A-B show a schematic view of an electrode paddle of the system with specifically activated electrodes for stimulation for walking with an ambulatory walker.

FIG. 8A shows a schematic view of the electrode paddle 19 of the system 10 with specifically activated electrodes for stimulation for walking with an ambulatory walker.

Figure 8B:
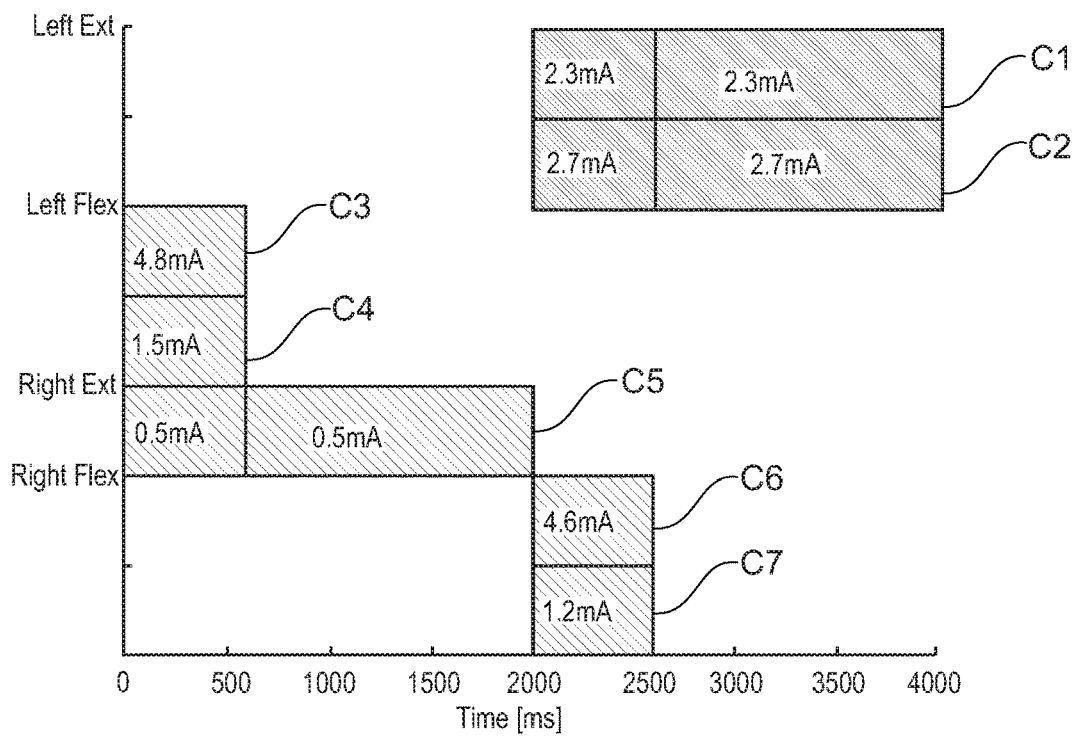

FIG. 8B shows in greater detail the respective sequences, the specific current and also the time span for right flexion stimulation, right extension stimulation, left flexion stimulation and left extension stimulation.

Stage C1 indicates in FIG. 8A and FIG. 8B the stimulation for left ankle extension, where FIG. 8A shows the activated (dark colored) and non-activated (white) electrodes and FIG. 8B shows the stimulation over time (2.3 mA for 2000 ms between 2000 ms to 4000 ms in the time span between 0 ms to 4000 ms).

Stage C2 indicates in FIG. 8A and FIG. 8B the stimulation for left knee extension, where FIG. 8A shows the activated (dark colored) and non-activated (white) electrode(s) and FIG. 8B shows the stimulation over time (2.7 mA for 2000 ms between 2000 ms to 4000 ms in the time span between 0 ms to 4000 ms).

Stage C3 indicates in FIG. 8A and FIG. 8B the stimulation for left hip flexion, where FIG. 8A shows the activated (dark colored) and non-activated (white) electrode(s) and FIG. 8B shows the stimulation over time (4.8 mA for 500 ms between 0 ms to 500 ms in the time span between 0 ms to 4000 ms).

Stage C4 indicates in FIG. 8A and FIG. 8B the stimulation for left ankle flexion, where FIG. 8A shows the activated (dark colored) and non-activated (white) electrode(s) and FIG. 8B shows the stimulation over time (1.5 mA for 500 ms between 0 ms to 500 ms in the time span between 0 ms to 4000 ms).

Stage C5 indicates in FIGS. 8A and 8B the stimulation for right ankle extension, where FIG. 8A shows the activated (dark colored) and non-activated (white) electrode(s) and FIG. 8B shows the stimulation over time (0.5 mA for 2000 ms between 0 ms to 2000 ms in the time span between 0 ms to 4000 ms).

Stage C6 indicates in FIGS. 8A and 8B the stimulation for right hip flexion, where FIG. 8A shows the activated (dark colored) and non-activated (white) electrode(s) and FIG. 8B shows the stimulation over time (4.6 mA for 500 ms between 2000 ms to 2500 ms in the time span between 0 ms to 4000 ms).

Stage C7 indicates in FIGS. 8A and 8B the stimulation for right ankle flexion, where FIG. 8A shows the activated (dark colored) and non-activated (white) electrode(s) and FIG. 8B shows the stimulation over time (1.2 mA for 500 ms between 2000 ms to 2500 ms in the time span between 0 ms to 4000 ms).

Figure 9A:
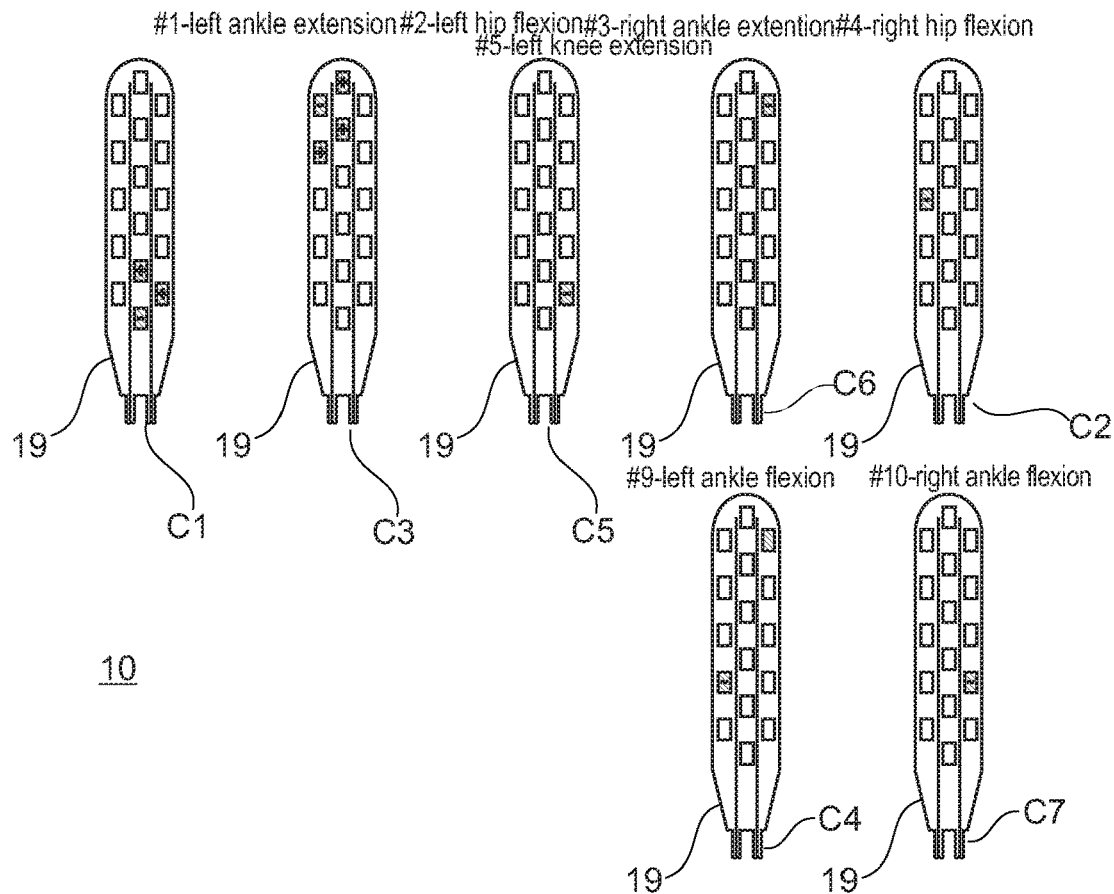
FIGS. 9A-B show a schematic view of an electrode paddle of the system with specifically activated electrodes for stimulation for walking at an enhanced rehabilitation stage (challenging scenario).

FIG. 9A shows a schematic view of an electrode paddle 19 of the system 10 with specifically activated electrodes (dark colored) for stimulation for walking at an enhanced rehabilitation stage (challenging scenario).

Figure 9B:
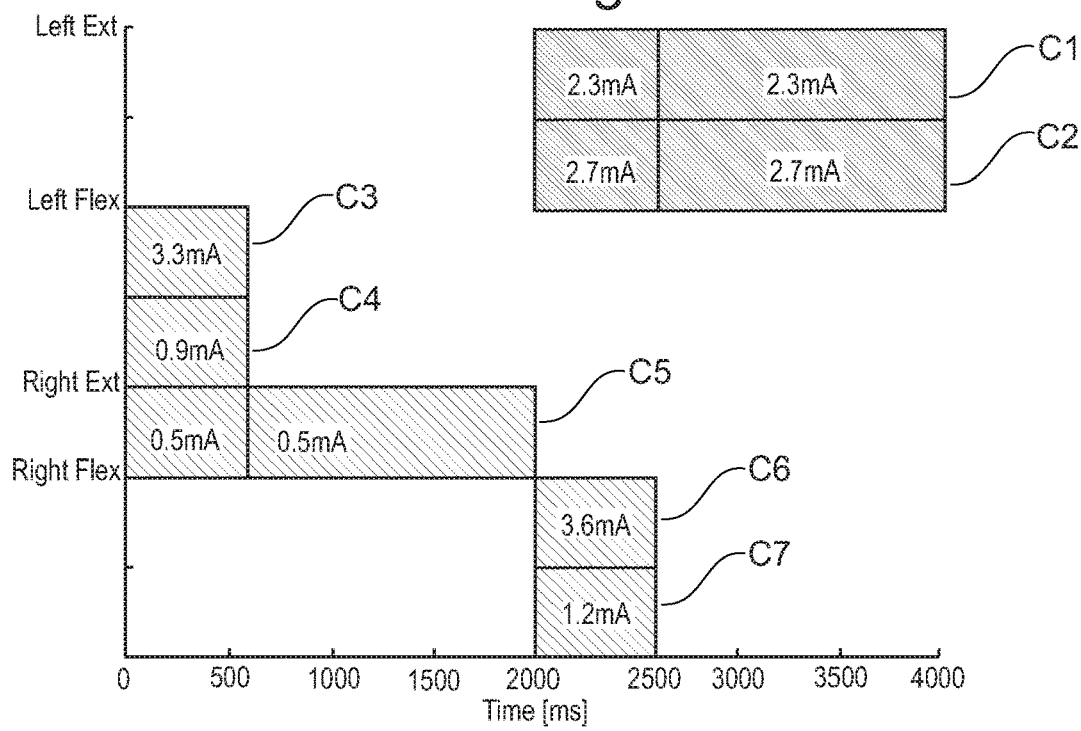

FIG. 9B shows in greater detail the respective sequences, the specific current and also the time span for right flexion stimulation, right extension stimulation, left flexion stimulation and left extension stimulation. For FIGS. 9A-9B, the various stages (C1-C7) are as described above with regard to FIGS. 8A-8B.

Figure 10A:
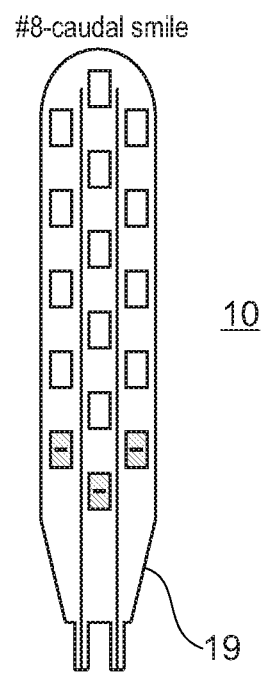
FIGS. 10A-B show a schematic view of an electrode paddle of the system with specifically activated electrodes for sacral stimulation to improve sexual function and bladder function.

FIG. 10A shows a schematic view of an electrode paddle 19 of the system 10 with specifically activated electrodes (dark colored) for sacral stimulation to improve sexual function and bladder function.

Figure 10B:
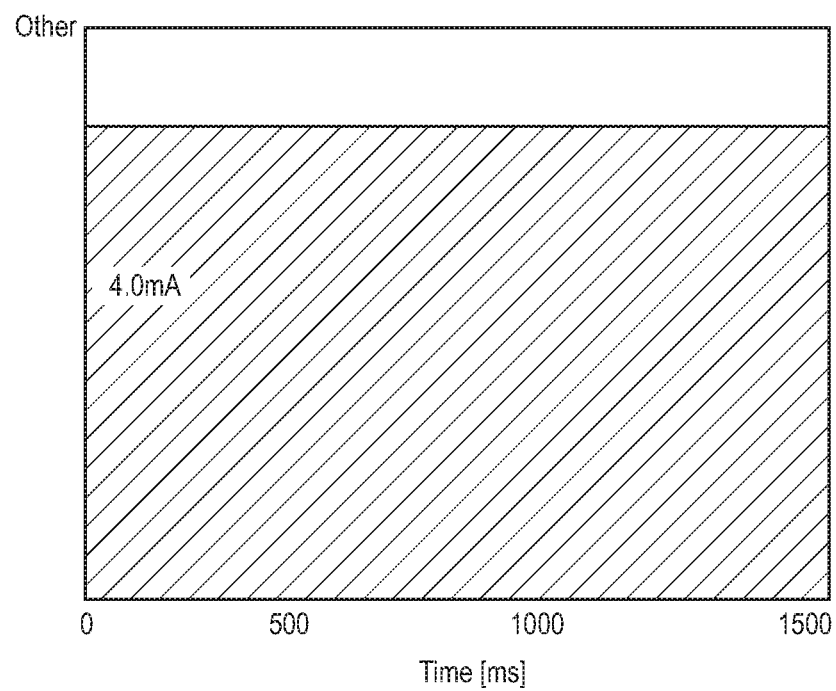

As can be derived from FIG. 10B, specific caudal stimulation for sacral stimulation to improve sexual function and bladder function is done for with a current of 4.0 mA for 1500 ms.

FIG. 11A shows a schematic view of the electrode paddle 19 of the system 10 with specifically activated electrodes (dark colored) for knee extension stimulation to facilitate sit-to-stand scenarios.

As can be derived from FIG. 11B, specific stimulation for right knee extension and specific stimulation for left knee extension is done at the same time with a current of 3.5 mA for 1000 ms.

Figure 12A:
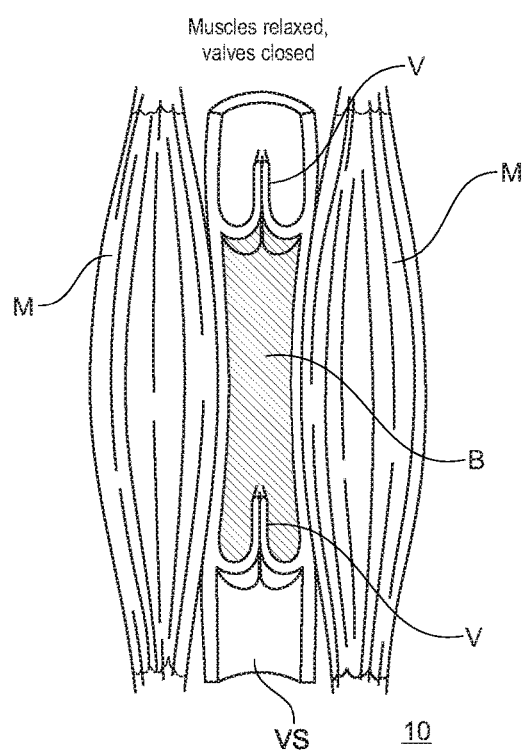
FIGS. 12A-B show a schematic view of the principle of a skeletal muscle pump by using the system according to FIG. 1.
Figure 12B:
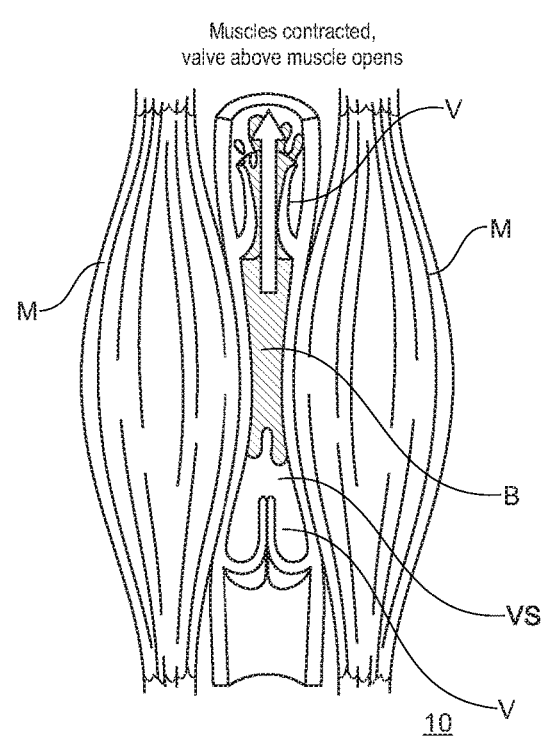

As shown in FIG. 12A and FIG. 12B, the system 10 provides a skeletal muscle pump in order to control the blood pressure of the patient.

Here, stimulation data SD comprise a sequence of stimulation patterns exploiting the skeletal muscle pump for blood pumping from the lower extremities of the subject in the direction back to the heart of the subject.

More specifically, the sequences comprise at least a first sequence related to stimulation of a muscle M in at least one extremity to relax the muscle M (cf. FIG. 12) and at least a second sequence related to stimulation of a muscle in this extremity to contract the muscle, which means that there is less or even no stimulation provided by the system 10 (FIG. 12B).

By this, it may be possible to assist the subject with blood pressure control and to avoid a blood pressure drop when the subject or patient wants to stand up, e.g. for starting to walk or the like. Also during walking such kind of stimulation may help the patient to perform his/her training.

In other words, open-loop phasic stimulation may be provided by the system to activate the Skeletal-muscle pump for counteracting orthostatic hypotension:

When a person rises from a horizontal to a vertical position, blood pools in the lower extremities, and blood pressure decreases. As a response, cardiac, vascular, neurological, muscular, and neurohumoral responses must occur quickly to increase and maintain blood pressure.

If any of these responses are abnormal, e.g., due to a neurological condition, blood pressure and organ perfusion may be reduced. In individuals with spinal cord injury, blood pressure may significantly decrease upon changing body position from a supine position to an upright posture, the physical effect called orthostatic hypotension. As a result, symptoms of central nervous system hypoperfusion may occur, including feelings of weakness, nausea, headache, neck ache, dizziness, blurred vision, fatigue, tremulousness, palpitations, and impaired cognition.

In turn, this may have a negative impact upon the ability of spinal cord injured individuals to participate in rehabilitation, such as stretching muscle-tendon complexes in a standing position using a standing frame, or participating to active standing training. In individuals with intact nervous system function, the skeletal-muscle pump aids the heart in the circulation of blood. Muscle contraction in the legs and abdomen compresses veins.

Because veins are equipped with one-way valves V (see FIG. 12A and FIG. 12B), blood B in the venous system VS is moved back to the heart. To illustrate the movement of the volume of blood B trapped between the two valves V (cf. FIG. 12A), only this volume is hatched/shaded (of course, the blood vessel is in the physiological state completely filled with blood B).

This physical effect through open-loop stimulation may be used to counteract orthostatic hypotension in individuals with spinal cord injury.

Stimulation may be set up to generate alternating muscle contractions and relaxations in the main antigravity and extensor muscles, for example the calf muscles.

Contraction and relaxation times may be chosen to be similar to those during slow walking.

Left-right alternating stimulation may be used to decrease simultaneously occurring extension forces that would periodically lift up and down the patient.

TABLE 1

Effect of open-loop phasic stimulation on blood pressure and heart rate (example embodiment)

| Time point of measure (mm:ss) | Body position | Blood pressure (upper/lower mmHg) | Heart rate (bpm) | Stimulation condition |
|---|---|---|---|---|
| 0' | Sitting Transition to standing frame | | | Stimulation off |
| 1' | Standing in the standing frame | 91/59 | 99 | |
| 1'55" | | 103/53 | 88 | |
| 2'40" | | 93/52 | 90 | |
| 3'50" | | 98/53 | 91 | |
| 5'00" | | 107/59 | 83 | Stimulation on |
| 7'00" | | 117/59 | 79 | |
| 8'00" | | 117/70 | 76 | |
| 9'00" | | 116/74 | 77 | |
| 11'00" | | 117/71 | 80 | |
| 12'10" | | 116/69 | 80 | |

Table 1 shows the effect of open-loop phasic stimulation on blood pressure and heart rate after changing body position in an individual with a low-cervical, chronic, sensory and motor incomplete spinal cord injury according to an example setup and example embodiment. Other embodiments are generally possible.

Alternating stimulation was applied through the left and right electrodes at the caudal end of an epidurally placed array, which were active for 1500 ms each in a free run mode (open-loop mode).

The electrode paddle with electrodes (cf. FIG. 4A-D, showing a corresponding electrode paddle 19 with electrodes 18*a*) was placed over the lumbar and upper sacral spinal cord segments, corresponding here to the T12 to L1 vertebral levels.

Stimulation frequency was 100 Hz, and amplitude was set at a level that generated alternating contractions in the left and right lower limb, predominantly in the calf and hamstrings muscle groups.

Furthermore, the stimulation data SD comprise a sequence of stimulation patterns for bringing back the sweating function is specific body part of the patient by increasing the excitability of the underlying neural circuits of said body part of the patient at the level of the spinal cord, translesionally, or at supraspinal levels.

Individuals with spinal cord injury are normally not fully able to adjust their body temperature below the level of the injury. One reason is that their sweating function is compromised below the injury level, likely because the brain (the hypothalamus) does not receive the necessary message that body temperature needs to be corrected. Symptoms of being too warm include nausea, headache, tiredness, reduced concentration, low blood pressure, and autonomic dysreflexia. In an individual with a chronic incomplete, low-cervical SCI the return of sweating function first in the feet could be observed, followed in the anterior and posterior trunk, and finally in the legs in the course of intensive locomotor training with phasic open-loop epidural spinal cord stimulation. Thus, phasic open-loop stimulation functions as an essential component in the return of sweating function after spinal cord injury, either by increasing the excitability of the underlying neural circuits at the level of the spinal cord (translesionally, or at supraspinal levels), and by the intense physical training over a prolonged period of time made possible by the open-loop stimulation.

As already mentioned above, the system 10 as shown in connection with FIG. 1 to FIG. 12B may be an open-loop system.

With such an open-loop system open-loop phasic stimulation may be provided. In contrast to closed-loop systems, open-loop may be understood such that neuromodulation and/or neurostimulation is provided, but the feedback from the patient is not used or does not influence the stimulation data. Also, the stimulation provided by the stimulation device, inter alia the sequences provided, is/are maintained. This may allow a simplified and reliable system. Also, the system may be less complex. It may form an additional system and/or supplement for existing systems or other systems.

For example, it may be possible that the system comprises and/or is connected and/or connectable with a closed-loop system for neuromodulation and/or neurostimulation.

Figure 13:
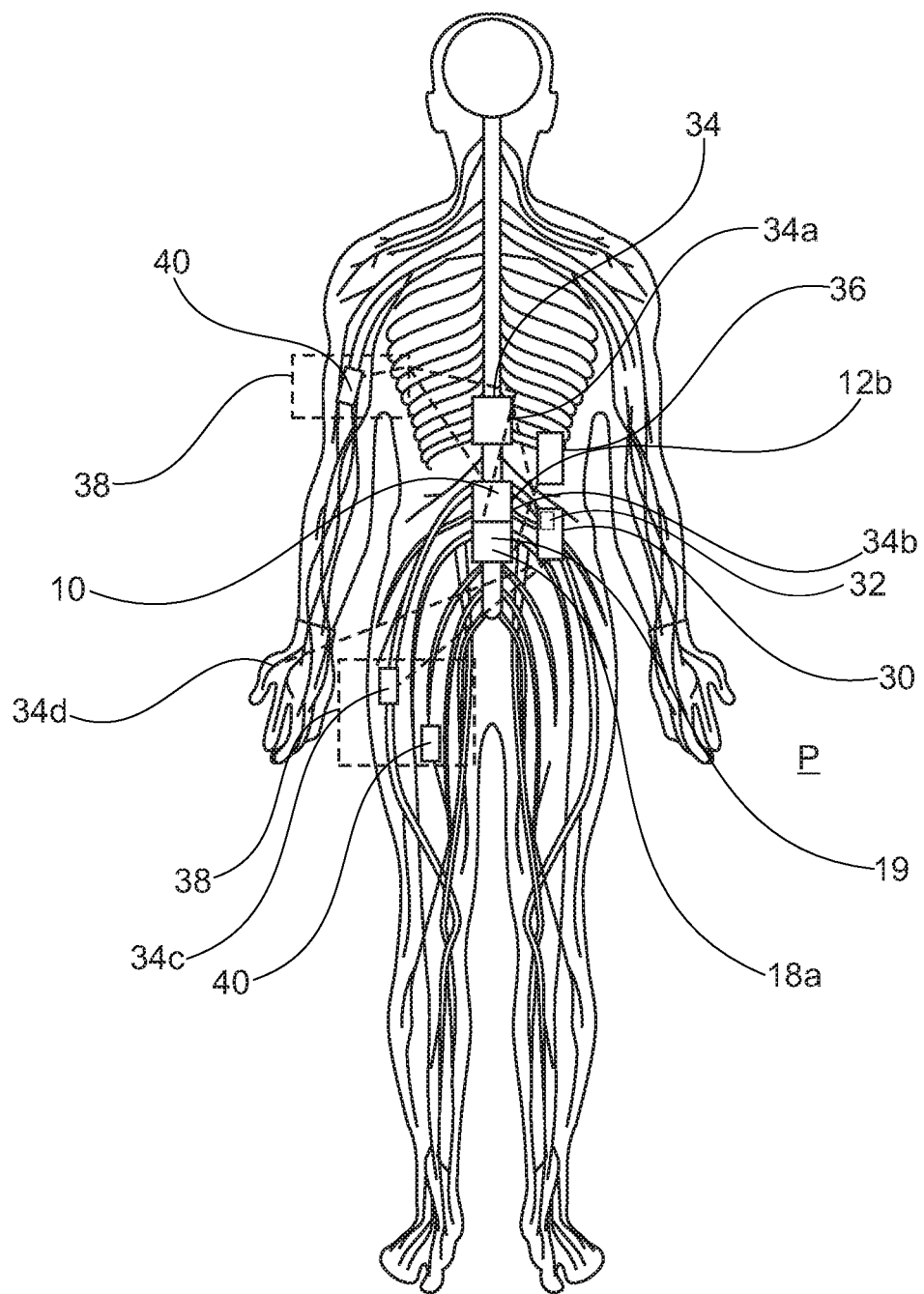
FIG. 13 shows a schematically view of the implanted system and the subject being equipped with the system FIG. 1 together with a closed loop system.

So, a combined closed-loop and open-loop system having an open-loop system 10 and a closed-loop system 30 can be provided as shown in FIG. 13.

The system 10 as shown in greater detail in FIG. 1 (components except the electrodes 18 not shown) with all components is implanted into the patient P.

The electrode paddle 19 with electrodes 18a is implanted into the spinal channel of the patient P in the lumbar region of the spinal cord.

There is also a controller 32 for the closed-loop system 30.

This controller 32 is connected to the system 10 via interface 12b.

The closed-loop system 30 has several sensors 34, 34a, 34b, 34c, 34d, wherein sensors 34, 34a, 34b, 34c are implanted sensors and sensor 34d is a wearable sensor (attached to hand by a glove).

Moreover, the closed-loop system 30 has a Central Nerve System (CNS) stimulation module 36, which may provide CNS stimulation via interface 12b to the electrode paddle 19 and the electrodes 18a.

There is also a Peripheral Nerve System (PNS) stimulation module 38, which is capable to provide PNS stimulation via at least one electrode 40 at a peripheral stimulation site.

The controller 32 receives signals from the various sensors 34, 34a, 34b, 34c, 34d and employs the various electrodes 18a, 40 of FIG. 13 to adjust stimulation parameters based on the received signals and instructions stored on a memory of the controller 32.

This allows the use of the open-loop approach for specific, predefined tasks, whereas the closed-loop approach may be used for other tasks, where the closed-loop approach promises more effect. A broader range of stimulation capabilities may be provided by such a combination.

In particular, the system 10 is for example here configured such that the stimulation data SD may be re-configured or adjusted on the basis of data being delivered by the closed-loop system. The re-configuration and/or adjustment may be done in real-time.

Closed-loop applications that depend on real-time kinematic parameters for enabling or inducing functional movement, e.g. locomotion, include the detection of some characteristic events of locomotion, e.g. a foot-off event to identify stance-to-swing transition or a certain position of the ankle with respect to the hip. Gait initiation is particularly difficult for individuals with severe SCI and compromises the quality of the gait event detection for the closed-loop system to further enable effective locomotion. We propose that open-loop stimulation will be critical to initiate the first steps in such patients, until the closed-loop system can extract critical information of the stepping and fully take over.

Therefore, the system 10 comprises the initialization module 22 and initialization data ID, wherein the initialization module 22 is configured and arranged to control the electrical stimulation device based on the initialization data such that the electrical stimulation device provides neuromodulation signals and/or neurostimulation signals, for an initialization action or movement of the subject. Especially, the system 10 as shown in FIG. 13 is configured and arranged such that the initialization module 22 and initialization data ID are used to start the closed-loop system 30.

Moreover, the open-loop stimulation provided by the system 10 may serve as a 'rescue mode' for closed-loop applications of the closed-loop system 30.

In case of continuous misdetections of the real-time system of a closed-loop application of the closed-loop system 30 or in the case of a very inconsistent gait, this will be detected by the controller 32 of the closed-loop system 30.

Then, control can be handed over to the controller 12 of the open-loop system, e.g. simply by (temporally) switching off the closed-loop system 30 or putting the closed-loop system 30 on hold or by re-booting the closed-loop system 30 or the like.

Thus, open-loop stimulation provided by the system 10 only is used until the closed-loop system 30 reliably detects gait events and takes over again. The switch between open- and closed-loop stimulation systems may be based on a gait event error detection system (such as inspection of the sequence of detected gait events).

Such a gait event error detection system may be a module of the closed-loop system 30 or may be installed or integrated into the controller 32 of the closed-loop system 30.

For these kinds of take over scenarios, the system 10 comprises a fallback module 24 and fallback module data FD, the fallback module data FD being specific stimulation data being stored in the stimulation pattern storage means, wherein the fallback module 24 is configured and arranged to control the electrical stimulation device 16 based on the fallback module data such that the electrical stimulation device provides neuromodulation signals and/or neurostimulation signals, for an actions or movement of the subject, when the closed-loop system is unintentionally out of service.

By this, the operational aspects of a closed-loop system may be increased and enhanced. In such a case, the system itself has the capability to provide open-loop stimulation and closed-loop stimulation or the system is combined with a closed-loop system. As open-loop stimulation does not include any feedback from the patient, such an approach is advantageous to maintain and provide at least basic stimulation capabilities, when closed-loop stimulation is temporarily not working.

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with the electronic control unit.

REFERENCES

10 Neuromodulation and/or neurostimulation system
11 Controller
12a Input means
12b Interface
14 Stimulation pattern storage means
14a Temporal stimulation pattern data storage module
14b Spatial stimulation pattern data storage module
14c Meta data storage module
16 Electrical stimulation device
18 Electrical interface
19 Electrode paddle
20 Bio-interface
22 Initialization module
24 Fallback module
30 Closed-loop system
32 Controller
34 Sensor
34a Sensor
34b Sensor
34c Sensor
34d Sensor
36 Central Nerve System (CNS) stimulation module
38 Peripheral Nerve System (PNS) stimulation module
40 Electrode
18* Activated Electrodes left flexion
18** Activated Electrodes right extension
18*** Activated Electrodes right flexion
18**** Activated Electrodes left extension
C1 Stage 1
C2 Stage 2
C3 Stage 3
C4 Stage 4
C5 Stage 5
C6 Stage 6
C7 Stage 7
S1 Step 1 of workflow for setting up an open-loop stimulation
S2 Step 2 of workflow for setting up an open-loop stimulation
S3 Step 3 of workflow for setting up an open-loop stimulation
S4 Step 4 of workflow for setting up an open-loop stimulation
S5 Step 5 of workflow for setting up an open-loop stimulation
SP1 Swing phase
SP2 Stance phase
SQ1 First sequence
SQ2 Second sequence
SQ3 Third sequence
SQ4 Fourth sequence
FD Fallback module data
ID Initialization data
SC Spatial component
SD Stimulation data
TC Temporal component
OS Onset of Stimulation
VI Volitional initiation of the first step
B Blood
VS Venous System
V One-way valve
P Patient

The invention claimed is:

1. A system for neuromodulation or neurostimulation, for the treatment of a subject, comprising:
at least a stimulation controller;
at least a stimulation pattern storage drive which is connected to the stimulation controller and which comprises stimulation data, the stimulation pattern storage drive comprises:
at least one spatial stimulation pattern data storage module for the spatial component;
at least one temporal stimulation pattern data storage module for the temporal component; and
wherein the stimulation controller is capable of accessing the modules or reading out the modules independently from each other;
at least one electrical stimulation device; and
at least one electrical interface between the at least one electrical stimulation device and the subject, the at least one electrical interface being connectable with at least one bio-interface of or with a nervous system of the subject;
wherein the at least one electrical interface and the at least one bio-interface or the nervous system are arranged such that signals and/or data are exchanged from the electrical interface to the bio-interface or vice versa,
wherein the stimulation controller is capable to send configuration signals on a basis of the stimulation data to the at least one electrical stimulation device such that via the at least one electrical interface an electrical stimulation is provided to the bio-interface,
wherein the electrical stimulation provided is characterized by one or more stimulation parameters that vary over time in a pre-programmed manner;
wherein the stimulation data represent pre-programmed patterns which comprise at least a spatial component which is related to a part of the nervous system being stimulated and a temporal component which is related to a time at which the spatial component is applied; and wherein the system is a combination of an open-loop stimulation and a closed-loop stimulation or may switch between the open-loop stimulation and the closed-loop stimulation.

2. The system of claim 1, wherein the one or more stimulation parameters is at least one of stimulation frequency, stimulation amplitude, stimulation current, or pulse width.

3. The system of claim 1, wherein the electrical stimulation device comprises a plurality of electrodes and wherein the spatial component comprises data related to activation and non-activation of defined subsets of the plurality of electrodes.

4. The system of claim 1, wherein the stimulation data comprises meta data, which link the spatial component and the temporal component to each other.

5. The system of claim 1, wherein the stimulation data comprises data representing a sequence of stimulation patterns adapted for bladder or sexual functions neurorehabilitation training, or for blood pressure control for counteracting orthostatic hypotension when the subject is verticalized or moves to a sitting position or a standing position or engages in sitting training or standing training.

6. The system of claim 5, wherein the sequence of stimulation patterns comprises a plurality of ordered stages which are arranged to form in their order a replication of physiological activation signals, the physiological activation signals including spinal activation signals for bladder or sexual functions neurorehabilitation training, or for blood pressure control for counteracting orthostatic hypotension when the subject is verticalized or moves to a sitting position or a standing position or engages in sitting training or standing training.

7. The system of claim 1, wherein the stimulation data comprises data representing a sequence of stimulation patterns exploiting a skeletal muscle pump for pumping blood from at least one extremity of the subject in a direction back to a heart of the subject, wherein the sequence comprises:
at least a first sequence related to stimulation of a muscle in the at least one extremity of the subject to contract the muscle; and
at least a second sequence related to stimulation of the muscle in the at least one extremity to relax the muscle.

8. The system of claim 1, wherein the open-loop stimulation is configured such that the stimulation data is capable of being re-configured or adjusted based on feedback data sensed by the system, wherein the re-configuration or adjustment is done in real-time.

9. The system of claim 1, wherein the stimulation data represents a sequence of stimulation patterns, wherein the sequence of stimulation patterns is a_-starting sequence.

10. The system of claim 1 further comprising:
at least one initialization module usable for open-loop stimulation; and
initialization data, the initialization data including stimulation data stored in the stimulation pattern storage drive;
wherein the at least one initialization module is configured and arranged to control the electrical stimulation device based on the initialization data such that the electrical stimulation device provides neuromodulation signals or neurostimulation signals for an initialization action or movement of the subject.

11. The system of claim 10, wherein the open-loop is configured and arranged such that the initialization module and initialization data are used to start the closed-loop stimulation.

12. The system of claim 1, wherein the open-loop system comprises:
at least one fallback module; and
fallback module data;
wherein the at least one fallback module is configured to control the electrical stimulation device based on the fallback module data when the closed-loop stimulation is out of service.

13. The system of claim 1, wherein the stimulation data represents a sequence of stimulation patterns adapted to help restore a sweating function in a body part of the subject.

14. A method for neuromodulation or neurostimulation for the treatment of a subject, comprising:
providing at least one electrical stimulation device; and
providing at least one electrical interface between the at least one electrical stimulation device and the subject;
connecting at least one neural interface between the subject to the at least one electrical interface; and
applying electrical stimulation using the at least one electrical stimulation device through the at least one electrical interface;
wherein the subject is stimulated with the at least one electrical stimulation device using stimulation pattern data, the stimulation pattern data represents pre-programmed patterns comprising:
a spatial component related to a part of a nervous system of the subject being stimulated; and
a temporal component related to a time at which each spatial component is applied;
wherein the electrical stimulation provided is characterized by stimulation parameters that vary over time in a pre-programmed manner; and
wherein the electrical stimulation is a combination of open-loop stimulation and closed-loop stimulation or may switch between the open-loop stimulation and closed-loop stimulation;
wherein the electrical stimulation is provided in one or more sequences, cyclically, or repeatedly:
wherein the one or more sequences comprise a plurality of ordered stimulation patterns which are arranged in that they form in their order a replication of phvsiological activation signals of particular muscle groups at an appropriate time for a specific task or movement of the subject;
wherein the speeific task or movement is at least one of walking, standing up, sitting down, climbing staircases, cycling, lifting a foot, or placing or moving an extremity or a head of the subject.

15. The method of claim 6, wherein the electrical stimulation stimulates at least one muscle of the subject for pumping blood from at least one extremity of the subject in a direction back to a heart of the subject.

16. The method of claim 15, wherein under conditions where the electrical stimulation stimulates the at least one muscle of the subject, the at least one muscle is stimulated to contract and relax alternately.

17. The method of claim 14, wherein the electrical stimulation stimulates at least one muscle of the subject to bring back a sweating function in a body part of the subject.

* * * * *